US010239051B2

(12) United States Patent
Haw et al.

(10) Patent No.: US 10,239,051 B2
(45) Date of Patent: Mar. 26, 2019

(54) CATALYST COMPOSITIONS COMPRISING SMALL SIZE MOLECULAR SIEVES CRYSTALS DEPOSITED ON A POROUS MATERIAL

(71) Applicants: TOTAL RESEARCH & TECHNOLOGY FELUY, Seneffe (BE); CENTRE NATIONAL DE LA RECHERCHE SCIENTIFIQUE (CNRS), Paris (FR)

(72) Inventors: Kok-Giap Haw, Muar Johor (MY); Jean-Michel Goupil, Le Marais la Chapelle (FR); Jean-Pierre Gilson, Cairon (FR); Valentin Valtchev, Basly (FR); Nikolai Nesterenko, Nivelles (BE); Delphine Minoux, Nivelles (BE); Jean-Pierre Dath, Beloeil (BE)

(73) Assignees: TOTAL RESEARCH & TECHNOLOGY FELUY, Seneffe (BE); CENTRE NATIONAL DE LA RECHERCHE SCIENTIFIQUE (CNRS, Paris (FR)

( * ) Notice: Subject to any disclaimer, the term of this patent is extended or adjusted under 35 U.S.C. 154(b) by 381 days.

(21) Appl. No.: 14/902,233

(22) PCT Filed: Jul. 3, 2014

(86) PCT No.: PCT/EP2014/064149
§ 371 (c)(1),
(2) Date: Dec. 30, 2015

(87) PCT Pub. No.: WO2015/001004
PCT Pub. Date: Jan. 8, 2015

(65) Prior Publication Data
US 2016/0136625 A1 May 19, 2016

(30) Foreign Application Priority Data

Jul. 4, 2013 (EP) .................................... 13175185

(51) Int. Cl.
*B01J 29/06* (2006.01)
*B01J 29/40* (2006.01)
(Continued)

(52) U.S. Cl.
CPC ............. *B01J 29/40* (2013.01); *B01J 29/00* (2013.01); *B01J 29/005* (2013.01); *B01J 29/041* (2013.01); *B01J 29/043* (2013.01); *B01J 29/405* (2013.01); *B01J 29/44* (2013.01); *B01J 35/0006* (2013.01); *B01J 35/0013* (2013.01); *B01J 35/023* (2013.01); *B01J 35/109* (2013.01); *B01J 35/1019* (2013.01); *B01J 35/1061* (2013.01); *B01J 35/1095* (2013.01); *B01J 37/0009* (2013.01); *B01J 37/0201* (2013.01); *B01J 37/0203* (2013.01); *B01J 37/0207* (2013.01); *B01J 37/0209* (2013.01); *B01J 37/0211* (2013.01); *B01J 37/0246* (2013.01); *B01J 37/08* (2013.01); *B01J 37/28* (2013.01); *C07C 4/18* (2013.01); *C10G 3/44* (2013.01); *C10G 3/45* (2013.01); *C10G 3/47* (2013.01); *C10G 11/02* (2013.01); *C10G 11/18* (2013.01); *C10G 29/205* (2013.01); *C10G 35/06* (2013.01); *C10G 35/085* (2013.01); *C10G 45/60* (2013.01); *C10G 45/62* (2013.01); *C10G 47/02* (2013.01);
(Continued)

(58) Field of Classification Search
CPC . B01J 29/40; B01J 29/44; B01J 29/041; B01J 29/043; B01J 29/045; B01J 29/005; B01J 29/405; B01J 2229/18; B01J 2229/20; B01J 2229/42; B01J 2229/64; B01J 2229/186; B01J 2229/62; B01J 35/1019; B01J 35/109; B01J 35/1061; B01J 35/0006; B01J 35/0013; B01J 35/023; B01J 37/08; B01J 37/28; B01J 37/0246; B01J 37/0009; B01J 37/0209; B01J 37/0201; B01J 37/0203; B01J 37/0207; B01J 37/0211; C07C 2529/40; C07C 2529/80; C07C 2529/068; C07C 2529/076; C07C 2529/44; C07C 2529/48
USPC .................................... 502/60, 63, 64, 66, 69
See application file for complete search history.

(56) References Cited

U.S. PATENT DOCUMENTS 3,308,069 A 3/1967 Wadlinger et al.
3,702,886 A 11/1972 Argauer et al.
(Continued)

FOREIGN PATENT DOCUMENTS

CN 1210883 A 3/1999
CN 101376838 A 3/2009
(Continued)

OTHER PUBLICATIONS

Machine translation of FR 2 981 943, May 3, 2013.*
(Continued)

*Primary Examiner* — Elizabeth D Wood
(74) *Attorney, Agent, or Firm* — Albert Shung

(57) ABSTRACT

A catalyst composition contains an inorganic porous material with pore diameters of at least 2 nm and of crystals of molecular sieve. The crystals of molecular sieve have an average diameter, measured by scanning electron microscopy, not bigger than 50 nm. The catalyst composition has a concentration of acid sites ranges from 50 to 1200 µmol/g measured by TPD NH3 adsorption. An XRD pattern of the catalyst composition is the same as an XRD pattern of the inorganic porous material.

12 Claims, 13 Drawing Sheets

(51) Int. Cl.

| | |
|---|---|
| *B01J 29/44* | (2006.01) |
| *B01J 29/04* | (2006.01) |
| *B01J 29/00* | (2006.01) |
| *B01J 37/02* | (2006.01) |
| *B01J 35/00* | (2006.01) |
| *B01J 35/02* | (2006.01) |
| *B01J 35/10* | (2006.01) |
| *B01J 37/00* | (2006.01) |
| *C10G 50/00* | (2006.01) |
| *C07C 4/18* | (2006.01) |
| *C10G 29/20* | (2006.01) |
| *C10G 35/06* | (2006.01) |
| *C10G 35/085* | (2006.01) |
| *C10G 45/60* | (2006.01) |
| *C10G 45/62* | (2006.01) |
| *C10G 47/02* | (2006.01) |
| *C10G 47/12* | (2006.01) |
| *C10G 3/00* | (2006.01) |
| *C10G 11/02* | (2006.01) |
| *C10G 11/18* | (2006.01) |
| *B01J 37/28* | (2006.01) |
| *B01J 37/08* | (2006.01) |

(52) U.S. Cl.
CPC ............ *C10G 47/12* (2013.01); *C10G 50/00* (2013.01); *B01J 2229/18* (2013.01); *B01J 2229/186* (2013.01); *B01J 2229/20* (2013.01); *B01J 2229/42* (2013.01); *B01J 2229/62* (2013.01); *B01J 2229/64* (2013.01); *C07C 2529/068* (2013.01); *C07C 2529/076* (2013.01); *C07C 2529/40* (2013.01); *C07C 2529/44* (2013.01); *C07C 2529/48* (2013.01); *C07C 2529/80* (2013.01); *Y02P 20/52* (2015.11); *Y02P 30/20* (2015.11)

(56) References Cited

U.S. PATENT DOCUMENTS

| | | |
|---|---|---|
| 3,709,979 A | 1/1973 | Chu et al. |
| 3,832,449 A | 8/1974 | Rosinski et al. |
| 3,948,758 A | 4/1976 | Bonacci et al. |
| 4,016,245 A | 4/1977 | Plank et al. |
| 4,076,842 A | 2/1978 | Plank et al. |
| 4,086,186 A | 4/1978 | Rubin et al. |
| 4,229,424 A | 10/1980 | Kokotailo |
| 4,254,297 A | 3/1981 | Frenken et al. |
| 4,310,440 A | 1/1982 | Wilson et al. |
| 4,397,827 A | 8/1983 | Chu |
| 4,440,871 A | 4/1984 | Lok et al. |
| 4,493,902 A | 1/1985 | Brown et al. |
| 4,500,651 A | 2/1985 | Lok et al. |
| 4,551,236 A | 11/1985 | Lok et al. |
| 4,554,143 A | 11/1985 | Messina et al. |
| 4,567,029 A | 1/1986 | Wilson et al. |
| 4,605,492 A | 8/1986 | Lok et al. |
| 4,619,818 A | 10/1986 | Derouane et al. |
| 4,623,527 A | 11/1986 | Derouane et al. |
| 4,632,811 A | 12/1986 | Derouane et al. |
| 4,639,357 A | 1/1987 | Derouane et al. |
| 4,639,358 A | 1/1987 | Derouane et al. |
| 4,664,897 A | 5/1987 | Derouane et al. |
| 4,673,559 A | 6/1987 | Derouane et al. |
| 4,683,217 A | 7/1987 | Lok et al. |
| 4,684,617 A | 8/1987 | Lok et al. |
| 4,686,092 A | 8/1987 | Lok et al. |
| 4,686,093 A | 8/1987 | Flanigen et al. |
| 4,698,217 A | 10/1987 | Valyocsik |
| 4,735,806 A | 4/1988 | Flanigen et al. |
| 4,737,353 A | 4/1988 | Flanigen et al. |
| 4,738,837 A | 4/1988 | Flanigen et al. |
| 4,744,885 A | 5/1988 | Messina et al. |
| 4,744,970 A | 5/1988 | Lok et al. |
| 4,758,419 A | 7/1988 | Lok et al. |
| 4,759,919 A | 7/1988 | Flanigen et al. |
| 4,781,814 A | 11/1988 | Flanigen et al. |
| 4,789,535 A | 12/1988 | Flanigen et al. |
| 4,793,833 A | 12/1988 | Lok et al. |
| 4,793,984 A | 12/1988 | Lok et al. |
| 4,797,267 A | 1/1989 | Kuehl |
| 4,801,309 A | 1/1989 | Lok et al. |
| 4,801,364 A | 1/1989 | Wilson et al. |
| 4,822,478 A | 4/1989 | Lok et al. |
| 4,824,554 A | 4/1989 | Lok et al. |
| 4,846,956 A | 7/1989 | Lok et al. |
| 4,851,106 A | 7/1989 | Flanigen et al. |
| 4,853,197 A | 8/1989 | Wilson et al. |
| 4,880,520 A | 11/1989 | Lok et al. |
| 4,880,611 A | 11/1989 | Von Ballmoos et al. |
| 4,882,038 A | 11/1989 | Lok et al. |
| 4,888,167 A | 12/1989 | Flanigen et al. |
| 4,894,213 A | 1/1990 | Flanigen et al. |
| 4,913,888 A | 4/1990 | Flanigen et al. |
| 4,917,876 A | 4/1990 | Lok et al. |
| 4,935,216 A | 6/1990 | Lok et al. |
| 4,940,570 A | 7/1990 | Flanigen et al. |
| 4,952,384 A | 8/1990 | Lok et al. |
| 4,954,325 A | 9/1990 | Rubin et al. |
| 4,956,164 A | 9/1990 | Lok et al. |
| 4,956,165 A | 9/1990 | Lok et al. |
| 4,973,460 A | 11/1990 | Flanigen et al. |
| 4,973,785 A | 11/1990 | Lok et al. |
| 4,992,250 A | 2/1991 | Flanigen et al. |
| 5,057,295 A | 10/1991 | Flanigen et al. |
| 5,098,684 A | 3/1992 | Kresge et al. |
| 5,102,643 A | 4/1992 | Kresge et al. |
| 5,108,725 A | 4/1992 | Beck et al. |
| 5,198,203 A | 3/1993 | Kresge et al. |
| 5,236,575 A | 8/1993 | Bennett et al. |
| 5,241,093 A | 8/1993 | Joly et al. |
| 5,278,345 A | 1/1994 | Janssen et al. |
| 5,336,478 A | 8/1994 | Dwyer et al. |
| 5,345,011 A | 9/1994 | Durante et al. |
| 5,362,697 A | 11/1994 | Fung et al. |
| 5,434,326 A | 7/1995 | Gajda et al. |
| 5,478,787 A | 12/1995 | Dandekar et al. |
| 5,493,066 A | 2/1996 | Kraushaar-Czarnetzki et al. |
| 5,675,050 A | 10/1997 | Des Courieres et al. |
| 5,783,321 A | 7/1998 | Verduijn et al. |
| 5,972,203 A | 10/1999 | Smith et al. |
| 6,156,931 A | 12/2000 | Lewis |
| 6,284,696 B1 | 9/2001 | Koya et al. |
| 6,300,535 B1 | 10/2001 | Van Den Berge et al. |
| 2004/0192947 A1* | 9/2004 | Chane-Ching ........... B01J 29/03 549/533 |
| 2005/0181933 A1 | 8/2005 | Ku et al. |
| 2006/0182681 A1* | 8/2006 | Kumar ................. B01J 29/005 423/700 |
| 2009/0036294 A1* | 2/2009 | Bouizi ..................... B01J 29/80 502/60 |
| 2009/0156389 A1* | 6/2009 | Ryoo ....................... B01J 29/40 502/64 |
| 2009/0266237 A1* | 10/2009 | Serra Alfaro ........ B01D 53/228 96/154 |
| 2009/0270245 A1* | 10/2009 | Kumar .................. B01J 29/005 502/60 |
| 2012/0024776 A1* | 2/2012 | Garcia-Martinez ...... B01J 20/18 210/500.25 |
| 2013/0105363 A1 | 5/2013 | Batalha et al. |
| 2014/0027346 A1* | 1/2014 | Chaumonnot ......... B01J 29/005 208/89 |

FOREIGN PATENT DOCUMENTS

| | | |
|---|---|---|
| EP | 0158350 A2 | 10/1985 |
| EP | 0158975 A2 | 10/1985 |
| EP | 0158976 A2 | 10/1985 |
| EP | 0159624 A2 | 10/1985 |
| EP | 0161489 A1 | 11/1985 |

(56) References Cited

FOREIGN PATENT DOCUMENTS

| EP | 0229295 A2 | 7/1987 |
|---|---|---|
| EP | 0293937 A2 | 12/1988 |
| FR | 2981943 A1 | 5/2013 |
| GB | 1060749 A | 3/1967 |
| WO | 9512454 A | 5/1995 |
| WO | 9857743 A2 | 12/1998 |
| WO | 2006105771 A1 | 10/2006 |

OTHER PUBLICATIONS

J. Rouquerol et al., "Recommendations for the characterization of porous solids (Technical Report)" International Union of Pure and Applied Chemistry (IUPAC); Pure & Appl. Chem., (1994), vol. 66, No. 8, pp. 1739-1758.

L. B. McCusker et al., "Nomenclature of structural and compositional characteristics of ordered microporous and mesoporous materials with inorganic hosts (IUPAC Recommendations 2001)" Pure Appl. Chem., (2001), vol. 73, No. 2, pp. 381-394.

Ullmann's Encyclopedia of Industrial Chemistry, 6th completely revised edition, vol. 14, 2003, pp. 201-212.

Ullmann's Encyclopedia of Industrial Chemistry, 6th completely revised edition, vol. 11, 2003, pp. 702-711.

International Search Report issued in PCT/EP2014/064149, dated Sep. 30, 2014, 5 pages.

Rajendra Srivastava et al, "Synthesis of Nanocrystalline MFI-Zeolites with Intracrystal Mesopores and Their Application in Fine Chemical Synthesis Involving Large Molecules", Chemistry—A European Journal, (Oct. 29, 2008), vol. 14, No. 31, pp. 9507-9511.

Jacobsen C J H et al, "Zeolites by confined space synthesis—characterization of the acid sites in nanosized ZSM-5 by ammonia desorption and 27Al/29Si-MAS NMR spectroscopy", Microporous and Mesoporous Materials, Elsevier Science Publishing, New York, US, (Sep. 1, 2000), vol. 39, No. 1-2, pp. 393-401.

Schmidt I et al, "Confined Space Synthesis. A Novel Route to Nanosized Zeolites", vol. 39, No. 11, (Apr. 20, 2000), pp. 2279-2283, Inorganic Chemistry, American Chemical Society, Easton, US.

Mavrodinova V et al, "Beta zeolite colloidal nanocrystals supported on mesoporous MCM-41", Journal of Colloid and Interface Science, Academic Press, New York, NY, US, (Jun. 1, 2005), vol. 286, No. 1, pp. 268-273.

Xu X et al, "Micrometer-scale macroporous silica-alumina composites with spheric and lathy MFI-type crystals via seed-induced in-situ and layer-by-layer synthetic methods", Materials Letters, North Holland Publishing Company. Amsterdam, NL, vol. 64, No. 15, (Aug. 15, 2010), pp. 1660-1663.

Office Action issued in Chinese Application No. 201480048382.3, dated Mar. 30, 2017, 17 pages.

\* cited by examiner

CATALYST COMPOSITIONS COMPRISING SMALL SIZE MOLECULAR SIEVES CRYSTALS DEPOSITED ON A POROUS MATERIAL

CROSS-REFERENCE TO RELATED APPLICATIONS

This application is a National Stage Entry of PCT/EP2014/064149, filed on Jul. 3, 2014; which claims priority to EP 13175185.1, filed on Jul. 4, 2013; the entireties of which are incorporated herein by reference.

FIELD OF THE INVENTION

The invention relates to catalyst compositions for hydrocarbon conversion comprising molecular sieves such as crystalline metallosilicate or zeolite. In particular, the invention relates to catalyst compositions comprising crystals of molecular sieve and porous material. The invention also relates to the preparations and the uses of said catalyst compositions.

PRIOR ART DESCRIPTION

Molecular sieves such as crystalline metallosilicates or zeolites have been demonstrated to possess catalytic properties for various types of hydrocarbon conversions. More precisely, the zeolites have been used as adsorbents, catalysts, and catalyst carriers for various types of hydrocarbon conversion processes, and other applications. They exhibit unique properties with respect to both catalytic activity and selectivity.

The catalytic activity of molecular sieves is related to their acidic properties and reflects the quantity of converted reactive per units of time.

Selectivity is the molar fraction of a particular wanted product over all the products formed. It is dependant of the micropores ranging in size from 3 Å to 12 Å. The shape and size of the micropores induce various kinds of shape selectivity. Besides the highly favorable role in providing shape selectivity, the presence of micropores may in some cases also, limit the catalytic performance of molecular sieves such as zeolites. Cause for this is the restricted molecular transport rate inside the molecular sieve crystal, induced by the similarity between the size of the involved hydrocarbons and the micropore diameter. Moreover because molecular sieves show small size pores of microporous type (i.e. smaller than 2 nm), the accessibility of the active sites for bulky molecules is limited to the active sites present on the surface of the crystals of molecular sieves. In transformations of the bulky molecules, the effective low diffusivity in molecular sieve crystals limits the reaction rate and yields. Only the external surface of the crystal of molecular sieve and the acid sites located in pore mouths are accessible to react with bulky molecules. Use of small size crystals of molecular sieves such as zeolite allows, for a given mass of crystals, increasing the external surface and thus increasing the number of accessible sites for reacting with bulky molecules. In other words, smaller is the crystal size, bigger will be the surface area (BET) and more important will be quantity of active sites. Unfortunately small size crystals of molecular sieves are difficult to handle as they have the tendency to agglomerate when used to catalyze reactions. Moreover they do not have sufficient mechanical and attrition resistance to be used as catalyst.

To overcome this drawback, it is known to produce catalyst compositions by depositing a molecular sieve such as a zeolitic coating on a carrier. The carrier gives the required mechanical and attrition resistance to the catalyst compositions. It also allows dispersing the molecular sieve active sites, preferably the zeolitic active sites, over its surface. Literature related to such catalyst compositions is relatively abundant in the field of fluid catalytic cracking (FCC) catalysts. In this field, the carrier usually used is non porous.

GB 1 060 749 relates to a catalyst comprising two components, one of which is used as carrier and is a particle form solid material which is catalytic or catalytically inert ranging generally from 200 mesh upwardly to 0.1 inch in diameter, the second component comprising a zeolitic molecular sieve conversion catalyst. The zeolitic molecular sieve in the form of particles ranging downward in diameter from 15 microns, having at least some material of not more than 5 microns in diameter and sufficient of said second component to substantially coat the particles of the first named component and to adhere to the surfaces of the particles of the first named component. The surface specific of the catalyst prepared is of 132 $m^2/g$.

US 2005/0181933 discloses a method of forming a zeolite of the ZSM-5 type comprising reacting calcinated kaolin microspheres with silicate and a seed solution used for forming zeolite Y under conditions of pH, temperature, and time to yield ZSM-5 crystals formed in-situ on said calcined kaolin microspheres. The carrier used is calcinated kaolin microspheres having a minimum of reactive alumina. The presence of ZSM-5 crystals is evidenced via X-ray diffraction (XRD).

WO 95/12454 discloses a process for making improved zeolitic FCC catalysts by spray drying a mixture of kaolin and spinel. The mixture is essentially free from metakaolin. The resulting microspheres are calcined to convert the hydrous kaolin to metakaolin. Then, they are reacted with a seeded alkaline sodium silicate solution in order to form zeolite crystals. The carrier used is metakaolin which is not a porous material. The presence of Y-faujasite zeolite crystals is evidenced via X-ray diffraction. In the examples, the surface area ranges from 230 $m^2/g$ to 330 $m^2/g$.

U.S. Pat. No. 4,493,902 describes fluid catalytic cracking catalyst (FCC) comprising microspheres containing more than about 40%, preferably 50-70% by weight of Y-faujasite zeolite. It also describes the method for making such catalysts. The catalyst is prepared via crystallization of Y-faujasite zeolite, originating from zeolite initiator, in microspheres derived from a mixture of metakaolin clay and kaolin clay. This document describes a large amount of zeolite coated on a material having no porosity. The presence of Y-faujasite zeolite crystals is evidenced via X-ray diffraction pattern.

Jacobsen C. J. H. et al. in "*Zeolites by confined space synthesis characterization of the acid sites in nanosized ZSM-5 by ammonia desorption and 27Al/29Si MAS NMR spectroscopy*" Microporous and Mesoporous materials vol. 39 no 1-2, 1 Sep. 2000 pages 393-401 described the preparation of ZSM-5 zeolite crystals in confined space. They crystallized small size crystal of zeolites inside the porosity of a carbon black matrix. The carbon black matrix is completely removed by calcinations in order to obtain finely dispersed crystals of ZSM-5. The crystals obtained finally are characterized by X ray diffraction and they show a clear XRD pattern signature of crystals of ZSM-5.

Schmidt I. et al. in: "*Confined space synthesis. A novel route to nanosized zeolites*" Inorganic chemistry, vol. 39 no 11, 1 Nov. 1990 pages 2279-2283 similarly described the preparation of zeolite crystals using a carbon black matrix to limit the crystal growth. The carbon black matrix is removed by calcinations. The crystals obtained are characterized by their X ray diffraction patterns and they show a clear XRD pattern of crystallized zeolite.

Srivastava R. et al, in: "*Synthesis of nanocrystalline MFI-zeolites with intracrystal mesopores and their application in fine chemical synthesis involving lager molecules*" Chemistry—A European Journal vol. 14 no 31, 29 Oct. 2008, pages 9507-9511 describes the preparation zeolite of the ZSM-5 type by controlling the nano-crystal size and mesoporosity by the addition of alkyl alkoxysilanes into conventional synthesis composition. The zeolite crystals obtained have a spherical/egg-shaped nanocrystalline morphology with a clear XRD pattern.

Xu X. et al in: "*micrometer scale macroporous silica alumina composites with spheric and lathy MFI-type crystals via seed-induced in-situ and layer-by-layer synthetic methods*" Materials Letters vol. 64, no 15, 15 Aug. 2010 pages 1660-1663 prepared a macroporous silica alumina composite material. They firstly prepared a silica alumina amorphous monolith that they impregnated afterward with a PDDA before being impregnated with a solution containing seeds of silica (silicalite-1 solution). The matrix covered with silica was finally converted into MFI using a vapor phase treatment (VPT) with the help of TPAOH template. The MFI structure was evidenced with a XRD and the SEM analysis of the crystal obtained showed the presence of spherical particles with the size of about 100 nm.

Mavrodinova V. et al. in: "Beta zeolite colloidal nanocrystal supported on mesoporous MCM-41" Journal of colloid and interface science, vol. 286, no 1, 1 Jun. 2005 used a preformed MCM-41 mesoporous molecular sieve on which they impregnated a beta zeolite nanophase. The beta zeolite was directly impregnated on the MCM-41 molecular sieve without the help of any other component. Once deposited, the zeolite beta was evidenced via XRD and acidity (measured via NH3 TPD) of the solid obtained was in the range of 2.01 to 2.97 mmol/g (i.e. 2010 to 2970 µmol/g).

WO 2006/105771 relates to membrane for gas separation prepared by impregnation of 4-, 6- and/or 8-ring zeolite over a porous substrate via impregnation (i.e. zeolites with a maximum pore diameter of 4.4 Å-0.44 nm). The impregnation is performed directly over the porous substrate without the help of any other components. Only small pore size zeolites are deposited over the materials because the main application of the membrane is gas phase separation. There is no application of the possible use of the membrane for catalytic reaction.

FR 2 981 943 describes the use of a hydrocracking catalyst prepared by zeolitisation of a porous mineral matrix. Zeolitisation is defined as putting into contact the matrix with source of element required for forming the zeolite followed by crystallisation of those elements under conditions to form the zeolite. The zeolite hence formed covered the surface of the matrix. Zeolitisation can be understood as a coating rather than a deposition of zeolite crystals. In particular, on page 9 line 19-21 it is stated that the beta zeolite forms a layer over the external surface of the porous mineral matrix or otherwise fills the porosity of the matrix. It can therefore be understood that zeolitisation leads to a coating of the matrix surface ant that a clearly defined crystallisation of zeolite is formed. Additionally in the example 2 page 15 line 5, it is stated that the crystallinity rate is of 95%.

The prior art provides us with catalyst compositions obtained by crystallization of a zeolite on different carriers, demonstrating the formation of the zeolitic phase by) XRD pattern signatures. This usually means forming zeolite of a crystal size in the range of 50 nm or more.

Alternatively the prior art describes the deposition of zeolite seeds or of zeolite precursor elements over a carrier followed by a step of crystal growth such as vapour phase transition. The zeolite crystals hence formed are evidenced via XRD.

It is known in the art to form zeolite crystals on a carrier such as kaolin using a zeolite precursor solution. The carrier is used to bring mechanical resistance to the catalyst. The carrier is generally constituted of small size particles having no porosity but agglomerated together. The catalyst is then constituted of this carrier covered with a coating of zeolite. The coating of zeolite consists in coverage of the surface of the carrier with a layer of crystalline zeolite. The uniform coating of the carrier with a zeolite layer is evidenced inter alia via X ray diffraction (XRD). The strong acidic sites of the zeolite present on the top of the zeolitic layer are accessible to small size and bulky molecules. The accessibility of the acidic sites located inside the zeolitic layer is hindered by diffusion limitation for small size molecule; for bulky molecules those acidic sites are not accessible.

An object of the invention is to provide catalyst compositions having an increased number of acidic sites both accessible for bulky and small size molecules.

Furthermore, it is a particular object of the present invention to provide a catalyst composition with an improved surface area. It is also a particular object of the present invention to provide catalyst compositions with improved activity and selectivity.

Another object of the invention is to provide a method to produce such catalyst composition.

There is also a need for stabilizing small size particles of crystals of molecular sieves while performing the catalyzed reactions.

BRIEF DESCRIPTION

In the following passages, different aspects of the invention are defined in more detail. Each aspect so defined may be combined with any other aspect or aspects unless clearly indicated to the contrary. In particular, any feature indicated as being preferred or advantageous may be combined with any other feature or features indicated as being preferred or advantageous.

Catalyst compositions having an increased number of acidic sites and also having acidic sites accessible both to bulky molecules and small size molecules have been discovered.

The invention provides a catalyst composition comprising a inorganic porous material with pore diameters of at least 2 nm and crystals of molecular sieve, remarkable in that: the crystals of molecular sieve have an average diameter not bigger than 50 nm measured using Scanning Electron Microscopy; the catalyst composition presents a concentration of acid sites ranging from 50 to 1200 µmol/g measured by TPD NH3 (Temperature-Programmed Desorption of ammonia); Bronsted acid sites concentration of at least 10 µmol/g measured by pyridine desorption at 150° C.; and X ray diffraction pattern of said catalyst composition is the same as the X ray diffraction pattern of said inorganic porous material. This final characteristic means that there is no change of the X ray diffraction pattern when the crystal of molecular sieves are being deposited on the inorganic porous material, it remains substantially the same. Deposition of crystal of molecular sieve is evidenced via indirect methods. For instance, the deposition of the crystal of molecular sieve is evidence by an increase of the surface area, an increase of the acidity or change in $^{27}$Al MAS NMR.

The catalyst composition according to the invention is further remarkable in that the inorganic porous material is amorphous. The use of an amorphous material renders more accessible the crystals of molecular sieve present in the catalyst composition because of its open porosity.

The catalyst composition according to the invention further remarkable in that it contains up to 30 weight % of crystals of molecular sieve relative to the total weight of the catalyst composition.

The catalyst compositions according to the invention is remarkable in that, the crystals of molecular sieve have an average diameter not bigger than 40 nm, preferably below 30 nm, even more preferably below 15 nm.

Presence of crystals of molecular sieve is also evidenced by an increase of the micro porous volume of the catalyst composition, compared to the carrier alone. Indeed the micro porous volume of the catalyst is mainly brought by the molecular sieve crystals.

Such acid concentration is high enough to perform reaction such as for instance cracking or oligomerization reactions.

The catalyst compositions according to the invention comprise a porous material with pore diameters of at least 2 nm and containing $Al_2O_3$ and $SiO_2$ with an atomic ratio Al/Si above 1, and up to 30 weight % of crystals of molecular sieve relative to the total weight of the catalyst composition.

The catalyst composition comprises at least 1 weight %, preferably 5 weight % most preferably 10 weight % of crystal of molecular sieves over the total catalyst composition weight.

The size of the crystals is such that they are not detectable by X-ray diffraction. However their presence is evidenced by the acidity of the catalyst compositions which is greater than the acidity of the porous material used as carrier alone. Acidity increases by at least 5%, preferably 10%, more preferably 20% measured by TPD NH3.

Preferably the catalyst compositions present a concentration of acid sites ranges from at least 200 µmol/g measured by TPD NH3, preferably at least 350 µmol/g.

Preferably the catalyst compositions present a concentration of acid sites ranges from at most 1000 µmol/g measured by TPD NH3, preferably at most 800 µmol/g.

Presence of crystals of molecular sieve is also evidenced by an increase of the micro porous volume of the catalyst composition, compared to the carrier alone. Indeed the micro porous volume of the catalyst is mainly brought by the molecular sieve crystals.

The catalyst compositions comprise microporous molecular sieves, but it remains substantially meso-macroporous. This means that the porous material having pores with a mesoporous volume and/or macroporous volume and the crystals of molecular sieve having pores with a microporous volume, the ratio of said microporous volume over the mesoporous and/or macroporous volume range from 0.2 cm$^3$/g to 0.005 cm$^3$/g said volumes being determined using ASTM D4365 (95-2008).

The surface area (measured using ASTM D3663) of the catalyst compositions is higher than the surface area of the porous material by at least 5%, preferably 10% more preferably 20% the most preferably 30%. The surface area is of at least 250 m$^2$/g, preferably at least 300 m$^2$/g even more preferably at least 350 m$^2$/g using ASTM D3663-03(2008).

The catalyst compositions being substantially meso-macroporous, this means that in the catalyst compositions has the ratio $V_{total}/V_{micro}$ of at least 5, more preferably higher than 10 with $V_{total}$ standing for the total porous volume (in cm$^3$/g) of the catalyst compositions and $V_{micro}$ standing for the microporous volume (in cm$^3$/g) of the catalyst compositions both being measured via ASTM D4365 (95-2008).

An important increase of the external surface area with a limited increase of the micro porous volume has the advantage that all the surface area added is accessible to bulky molecules and not in the micro porosity.

The acid sites concentration of the catalyst compositions is at least 10 µmol/g of acid sites as measured by pyridine adsorption. The acidity of the catalyst composition measured via pyridine adsorption at 150° C. is advantageously increased by at least 5%, preferably 10% more preferably 20% the most preferably 30% compared with the inorganic porous material alone.

Preferably the catalyst compositions present a concentration of Bronsted acid sites of at least at least 15 µmol/g, most preferably of at least 20 µmol/g measured by pyridine desorption at 150° C.

According to another embodiment, the catalyst composition is DRX amorphous. This means that the X ray diffraction pattern of the catalyst compositions does not present the characteristic bands of the crystal of molecular sieve, but it presents the DRX amorphous pattern of the porous material used as carrier. Indeed, in a preferred embodiment, the porous material is amorphous, more preferably the porous material contains a silica alumina, and more preferable the porous material is a high purity silica alumina material.

In another embodiment the catalyst composition according is remarkable in that the inorganic porous material is a silica alumina, a $SiO_2$, a $Al_2O_3$ or a mixture of thereof; or an amorphous inorganic material containing $Al_2O_3$ and $SiO_2$ with an atomic ratio Al/Si>1 with preference the porous material contains other elements different from Si, O, Al with a concentration below 500 ppm weight.

In another embodiment the catalyst composition according is also remarkable in that said crystals of molecular sieve is of MFI type, preferably of the ZMS-5 type.

In another embodiment, the catalyst composition is a shaped body in a form, which is directly suitable for the catalytic application in the fixed, moving, batch or fluidized bed reactors.

In another embodiment, the catalyst compositions further comprises one or more of:
 phosphorus;
 at least one metals selected from the group: B, Cr, Co, Ga, Fe, Li, Mg, Ca, Mn, La, Ti, Mo, Ni, Ag, Sn or Zn, Pt, Pd, Ru, Re, Os, Au or any combination thereof;
 at least one binder selected from silica, silica alumina, metal silicates, metal oxides such as ZrO2 and/or metals, amorphous alumophophate or silica alumophosphates, gels including mixtures of silica and metal oxides, amorphous alumophophate or any combination thereof.

In a preferred embodiment, the catalyst compositions contains crystals of molecular sieve with a pore diameter smaller than 2 nm preferably in the range of 0.3 to 1.2 nm, more preferably from 0.4 to 0.9 nm.

In another embodiment, the catalyst compositions contains crystals of molecular sieve with a pore diameter bigger than 0.3 or more preferably 0.5 nm and up to 0.9 nm preferably up to 1.1 nm most preferably up to 1.2 nm.

The catalyst compositions described above can be prepared by the following process of preparation that include the following steps:

a) providing an inorganic porous material;
b) optionally calcinating said porous material at temperature from 400° C. to 1200° C.;
c) providing a solution containing at least one charge surface modifying agent;
d) putting in contact the solution of step c) and the material obtained at step b) to obtain an amorphous inorganic porous material modified with a charge surface modifying agent;
e) providing a solution containing precursors for the molecular sieve;
f) reacting molecular sieves by:
  i) maturating during a period of time from 0 to 50 h the solution of step e), the maturating process being followed by DLS and stopped when crystals of molecular sieve have a maximum size of 50 nm, or preferably when the crystal of molecular sieve have a size in the range of 15 nm and subjecting a modified porous material in a contact with the maturated solution to deposit the molecular sieve crystals on the surface of the modified porous material obtained at step d); and/or
  ii) putting in contact said modified porous material obtained at step d) with the solution of step e) and maturating during a period of time from 0 to 50 h the obtained mixture until the acidity of the catalyst composition measured by TPD ammonia has increased of at least 10% compared with the acidity of the inorganic porous material; the maturation is stopped before crystal of molecular sieves appear on the X ray diffraction pattern of the catalyst composition.

The maturation time is adapted so that the X ray diffraction pattern of the inorganic porous material remains unchanged; i.e. the maturation time is increase to reach the desired the acidity of the catalyst composition but maturation is stopped before the molecular sieves appears on the X ray diffraction pattern, g) separating the solid from the liquid if any of the mixture obtained after step f);
h) calcinating the solid obtained at step g).

Advantageously the method of preparation presented above does not require particularly drastic operating condition to form the molecular sieve crystals. Indeed, the solution of step e) contains the entire element required for the molecular sieve preparation and there is no need of drastic condition to leach out of the amorphous inorganic porous material element necessary for forming the molecular sieve. There is no need of autoclave to increase the temperature and pressure in order to grow the molecular sieve crystals. There is no need to perform the deposition under vapour phase transition (VPT) conditions.

In another embodiment, the step e) to g) are repeated at least two times prior to performing h) in order to increase the content of crystals of molecular sieve deposited on the porous materials.

When steps e) to g) are repeated at least two times prior to performing h), preferably maturation of the solution is conducted for at least 30 min and at most 100 h each time, preferably at most 30 h, most preferably at most 20 h In another embodiment, the steps e) to g) are repeated at least two times prior to performing h), preferably maturation of the solution is conducted for at least 30 min and at most 100 h each time, preferably at most 30 h, most preferably at most 20 h even more preferably at most 10 h.

In another embodiment, the steps e) to g) are performed once and maturation of the solution is conducted for at least 10 h and preferably at least 30 h and most preferably at least 100 h.

In another embodiment, the steps e) to g) are performed once and maturation of the solution is conducted for at most 10 h and preferably at most 30 h and more preferably at most 20 h even more preferably at most 50 h.

In another embodiment the porous material contains $Al_2O_3$ and $SiO_2$ with an atomic ratio Al/Si>1 with preference the porous material contains other elements different from Si, O, Al with a concentration below 500 ppm weight.

In another embodiment, the catalyst compositions present the X ray pattern of the porous material, with preference the porous material is DRX amorphous.

In another embodiment, the process of preparation of catalyst compositions according to the invention may include one or more of the following steps, said steps being performed after step h) in any order:

introduction of phosphorous by impregnation of the catalyst composition by a solution containing phosphorous, said step being optionally followed by further steps of calcinations and/or steaming;

addition of at least one metal selected from the group: B, Cr, Co, Ga, Fe, Li, Mg, Ca, Mn, La, Ti, Mo, W, Ni, Ag, Sn or Zn, Pt, Pd, Ru, Re, Os, Au or any combination thereof, by impregnation of the catalyst compositions by a solution containing the selected metals salts;

addition of at least one binder selected from silica, silica alumina, metal silicates, metal oxides such as ZrO2 and/or metals, amorphous alumophophate or silica alumophosphates, gels including mixtures of silica and metal oxides, amorphous alumophophate or any combination thereof, by spray drying, extrusion or any suitable method known to the man skilled in the art;

shaping of the catalyst composition by extrusion.

In another embodiment, in the preparation of catalyst compositions according to the invention the porous material used is a high purity silica alumina.

Advantageously, the method of preparation of the catalyst can be performed directly on shaped catalyst or support or precursor. Indeed, the solution containing the crystals of molecular sieve can be impregnated on the catalyst being shaped in the form for instance of extrudates, spray-dried beads, spheres, tablets etc. In contrast to other techniques of synthesis of the micro-mesoporous materials, for example desilication, this modification leads to an increase of the surface area and acidity of the shaped bodies without destroying them. Additionally it simplifies the overall catalyst manufacturing process and represents significant economical advantages.

Examples of the reactions in which the catalyst compositions may be used, include but are not limited to: Fluid Catalytic Cracking, hydrocracking of heavy molecules, oligomerization of olefins, isomerisation, reforming of gasoline, alkylation, oxygenates conversion to hydrocarbon (methanol to olefins MTO, methanol to gasoline MTG, methanol to hydrocarbons MTH), dehydration of alcohols to corresponding olefins, olefins cracking, biomass conversion to olefins, biomass conversion to BTX (benzene, toluene, xylenes), biomass conversion to fuel, garbage transformation to fuel, hydrocracking of the extremely heavy feedstocks, monomers, chemicals, any kinds of catalytic pyrolysis or any reactions implying an organic component and requiring a catalyst acidic site or bifunctional site (acid and metallic functions).

The catalyst compositions according to the invention have an improved stability over time with still a high conversion and they are more selective.

The catalyst compositions according to the invention are equally useful for the conversion of bulky molecules, for the transformation of the small molecules to the bulky ones, like in oligomerization for the transformation occurred via a bulky transition intermediates.

The invention is also related to the catalyst compositions obtained by the process described above.

Another object of the invention is the use of the catalyst compositions in Fluid catalytic cracking reactions, catalytic pyrolysis of biomass, garbage, plastics derivates or their co-processing with conventional fossil feedstock's, hydrocracking of heavy hydrocarbons or extra heavy feedstocks, reactions of oligomerization of olefins, conversion of oxygenated molecules into to olefins, gasoline, aromatics or distillates, cracking of olefins toward lighter olefins, catalytic cracking of C4-C12 paraffin's, isomerisation reactions, reforming of gasoline, alkylation reactions, reactions of dehydration of alcohols to the corresponding olefins and/or dehydrogenation reactions.

DETAILED DESCRIPTION

Figure 1:
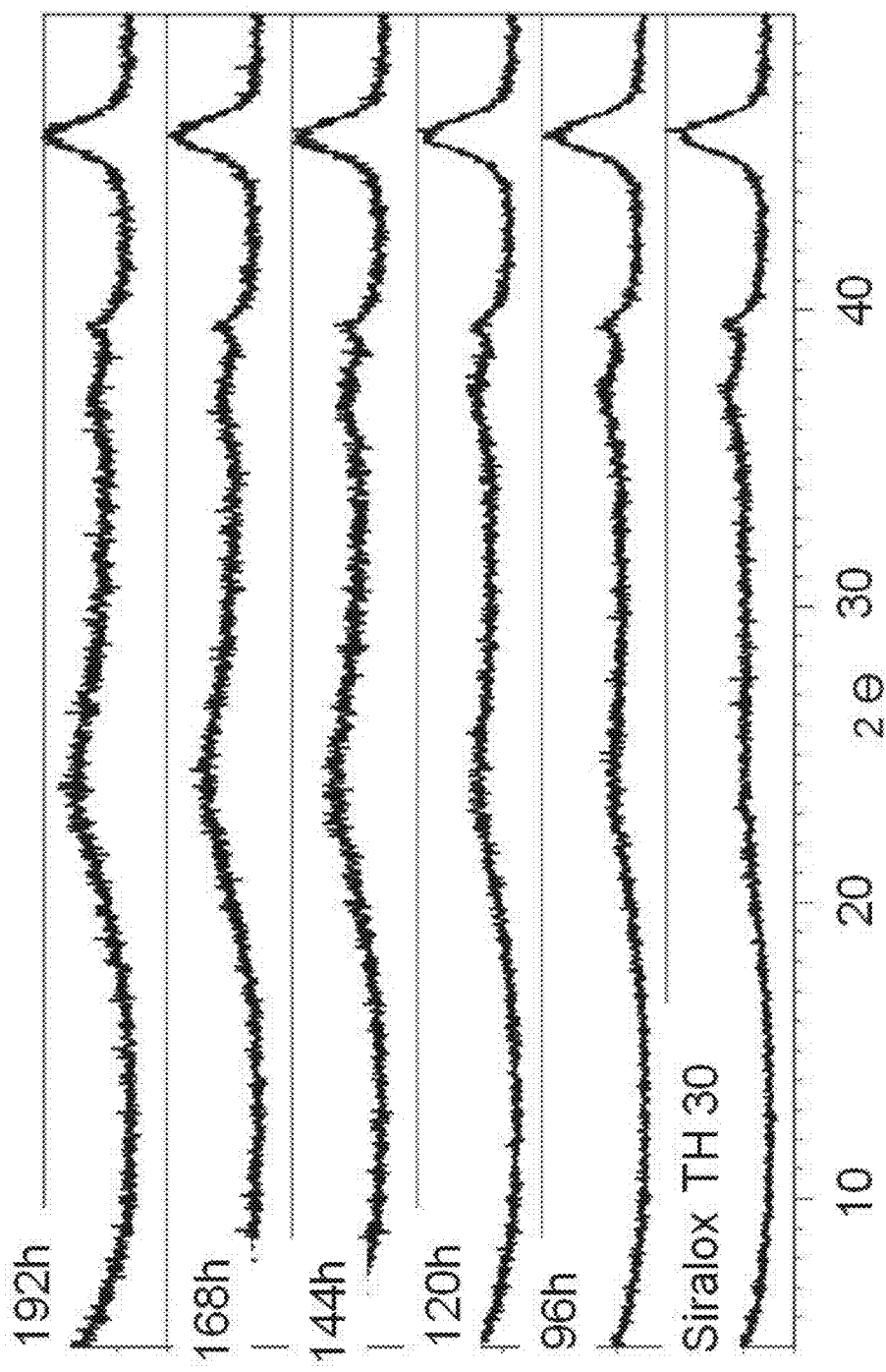
FIG. 1 presents the DRX patterns of the porous material prepared according to example 1.

As regards to the meaning of mesoporous, microporous and macroporous, as recommended by the International Union of Pure and Applied Chemistry (IUPAC) in *Pure & Appl. Chem.*, Vol. 66, No. 8, pp. 1739-1758, 1994, the term micropore refers to pore having a widths smaller than 2 nm; the term mesopore refers to pores with widths between 2 and 50 nm; the term macropore refers to pores with widths larger than 50 nm.

Detailed Description of the Catalyst Compositions Prepared

As regards to the catalyst compositions, it contains crystals of molecular sieve at a content ranging from 0.1 to 50 weight % of crystals of molecular sieve relative to the total weight of the catalyst compositions, more preferably in the range of 1 to 40 weight %, even more preferably in the range of 1 to 30 weight %. The catalyst compositions are characterized in that the crystals of molecular sieve are of a small size. The term "small" shall be understood as referring to particles having an average diameter smaller than 50 nm, preferably smaller than 40, more preferably smaller than 30 nm, most preferably of about 15 nm or below. The diameter of the crystals of molecular sieve is measured via scanning electron microscopy (SEM).

The present invention presents the advantage that the quantity of crystal of molecular sieves dispersed on the porous material can be adapted in order to tune the solid acidity for a given reaction. Therefore, the acidity of a given porous material can be increased to reach the desire activity to perform a given reaction. Determination of the adequate amount of crystals of molecular sieve to perform the reaction can be determined by simply testing the catalyst compositions prepared with the reaction considered.

Preferably, the molecular sieve crystal in accordance with the invention are dispersed over the surface of the carrier, and do not form a uniform layer coating the carrier as usual in the prior art. Indeed, with a coating, the only accessible sites are the sites present on the top of the layer. With dispersed molecular sieve crystals, sites present on the lateral sides of the crystal are additionally accessible. Consequently the dispersion of the crystals of molecular sieve leads to either an increase of the surface area, or of the micro porous volume or of the acidity or any combination of thereof. The dispersion of the molecular sieve crystals is facilitated by their small size i.e. by a diameter not bigger than 50 nm.

As regards to molecular sieve crystals, it can consist in any microporous materials having molecular sieve properties and advantageously presenting acidic active sites. More precisely they consist in crystallized material having pore diameter smaller than 2 nm, preferably pore diameter in the range of 1.2 to 0.3 nm. As none limiting example, one can cite aluminosilicate, metalsilicate; metalaluminophosphates (MeAlPO4) or crystalline microporous silicate.

They can consist in one embodiment of zeolite, which according to the invention is selected from the group MOR, FAU, EMM, MWW, BETA, ZSM-21, ZSM-42, AEI, CHA, ERI, LEV, OFF, ZSM-34, AFI, AEL, LTL, MFI (ZSM-5, silicalite, TS-1), MEL (ZSM-11, silicalite-2, TS-2), MTT (ZSM-23, EU-13, ISI-4, KZ-1), MFS (ZSM-57), HEU (Clinoptilolite), FER (ZSM-35, Ferrierite, FU-9, ISI-6, NU-23, Sr-D), TON (ZSM-22, Theta-1, ISI-1, KZ-2 and NU-10), LTL (L), MAZ (mazzite, Omega, ZSM-4) or a mixture thereof. These zeolites and their isotypes are described in the related literature. The structure types are provided by the IUPAC and can be found in Pure *Appl. Chem.*, Vol. 73, No. 2; pp. 381-394, 2001.

In an embodiment the zeolite structure is an intergrowth structure on the two or more phases, which according to invention could be selected from a group ZSM-34 (OFF/ERI), AEI/CHA, MFI/AEL etc.

Crystalline silicates are microporous crystalline inorganic polymers based on a framework of $XO_4$ tetrahedra linked to each other by sharing of oxygen ions, where X may be trivalent (e.g. Al, B, . . . ) or tetravalent (e.g. Ge, Si, . . . ). The crystal structure of a crystalline silicate is defined by the specific order in which a network of tetrahedral units is linked together. The size of the crystalline silicate pore openings is determined by the number of tetrahedral units, or, alternatively, oxygen atoms, required to form the pores and the nature of the cations that are present in the pores. They possess a unique combination of the following properties: high internal surface area; uniform pores with one or more discrete sizes; ion exchangeability; good thermal stability; and ability to adsorb organic compounds. Since the pores of these crystalline silicates are similar in size to many organic molecules of practical interest, they control the ingress and egress of reactants and products, resulting in particular selectivity in catalytic reactions. For instance, the crystalline silicates with the MFI structure possess a bidirectional intersecting pore system with the following pore diameters: a straight channel along [010]:0.53-0.56 nm and a sinusoidal channel along [100]:0.51-0.55 nm. Crystalline silicates with the MEL structure possess a bidirectional intersecting straight pore system with straight channels along [100] having pore diameters of 0.53-0.54 nm.

The metalsilicates obtained by the process of the present invention may comprise a charge balancing cation M selected from the group consisting of hydrogen, ammonium, monovalent, divalent and trivalent cations and mixtures thereof.

Molecular sieves, particularly zeolitic and zeolitic-type molecular sieves, preferably have a molecular framework of one, preferably two or more corner-sharing TO tetrahedral units, more preferably, two or more $SiO_4$, $AlO_4$ and/or $PO_4$ tetrahedral units. In particularly preferred embodiments, the molecular sieve framework can have two tetrahedral units of $SiO_4$ and $AlO_4$, or three tetrahedral units of $SiO_4$, $AlO_4$, and $PO_4$. These latter silicon, aluminum, and phosphorous based molecular sieves and metal containing silicon, aluminum and phosphorous based molecular sieves have been described in detail in numerous publications, including, for example, U.S. Pat. No. 4,567,029 (MeAPO where Me is Mg, Mn, Zn, or Co), U.S. Pat. No. 4,440,871 (SAPO), European Patent Application No. EP-A-O 159 624 (ELAPSO where El is As, Be, B, Cr, Co, Ga, Ge, Fe, Li, Mg, Mn, Ti or Zn), U.S. Pat. No. 4,554,143 (FeAPO), U.S. Pat. Nos. 4,822,478, 4,683,217, and 4,744,885 (FeAPSO), European Patent Application No. EP-A-O 158 975 and U.S. Pat. No. 4,935, 216 (ZnAPSO), European Patent Application No. EP-A-O 161 489 (CoAPSO), European Patent Application No. EP-A-O 158 976 (ELAPO, where El is Co, Fe, Mg, Mn, Ti or Zn), U.S. Pat. No. 4,310,440 (AlPO4), European Patent Application No. EP-A-0 158 350 (SENAPSO), U.S. Pat. No. 4,973,460 (LiAPSO), U.S. Pat. No. 4,789,535 (LiAPO), U.S. Pat. No. 4,992,250 (GeAPSO), U.S. Pat. No. 4,888,167 (GeAPO), U.S. Pat. No. 5,057,295 (BAPSO), U.S. Pat. No. 4,738,837 (CrAPSO), U.S. Pat. Nos. 4,759,919 and 4,851, 106 (CrAPO), U.S. Pat. Nos. 4,758,419, 4,882,038, 5,434, 326, and 5,478,787 (MgAPSO), U.S. Pat. No. 4,554,143 (FeAPO), U.S. Pat. No. 4,894,213 (AsAPSO), U.S. Pat. No. 4,913,888 (AsAPO), U.S. Pat. Nos. 4,686,092, 4,846,956, and 4,793,833 (MnAPSO), U.S. Pat. Nos. 5,345,011 and 6,156,931 (MnAPO), U.S. Pat. No. 4,737,353 (BeAPSO), U.S. Pat. No. 4,940,570 (BeAPO), U.S. Pat. Nos. 4,801,309, 4,684,617, and 4,880,520 (TiAPSO), U.S. Pat. Nos. 4,500, 651, 4,551,236, and 4,605,492 (TiAPO), U.S. Pat. Nos. 4,824,554 and 4,744,970 (CoAPSO), U.S. Pat. No. 4,735, 806 (GaAPSO), European Patent Application No. EP-A-O 293 937 (QAPSO, where Q is framework oxide unit [QO2]), as well as U.S. Pat. Nos. 4,567,029, 4,686,093, 4,781,814, 4,793,984, 4,801,364, 4,853,197, 4,917,876, 4,952,384, 4,956,164, 4,956,165, 4,973,785, 5,241,093, 5,493,066, and 5,675,050, all of which are herein fully incorporated by reference.

In one embodiment, the molecular sieves of the invention can be combined with one or more other molecular sieves. In another embodiment, the silicoaluminophosphate or aluminophosphate molecular sieves, or a combination thereof, can be combined with one more of the following non-limiting examples of molecular sieves, described in the following references: Beta (U.S. Pat. No. 3,308,069), ZSM-5 (U.S. Pat. Nos. 3,702,886, 4,797,267, and 5,783, 321), ZSM-1 (U.S. Pat. No. 3,709,979), ZSM-12 (U.S. Pat. No. 3,832,449), ZSM-12 and ZSM-38 (U.S. Pat. No. 3,948, 758), ZSM-22 (U.S. Pat. No. 5,336,478), ZSM-23 (U.S. Pat. No. 4,076,842), ZSM-34 (U.S. Pat. No. 4,086,186), ZSM-35 (U.S. Pat. No. 4,016,245, ZSM-48 (U.S. Pat. No. 4,397, 827), ZSM-58 (U.S. Pat. No. 4,698,217), MCM-I (U.S. Pat. No. 4,639,358), MCM-2 (U.S. Pat. No. 4,673,559), MCM-3 (U.S. Pat. No. 4,632,811), MCM-4 (U.S. Pat. No. 4,664, 897), MCM-5 (U.S. Pat. No. 4,639,357), MCM-9 (U.S. Pat. No. 4,880,611), MCM-10 (U.S. Pat. No. 4,623,527), MCM-14 (U.S. Pat. No. 4,619,818), MCM-22 (U.S. Pat. No. 4,954,325), MCM-41 (U.S. Pat. No. 5,098,684), M-41S (U.S. Pat. No. 5,102,643), MCM-48 (U.S. Pat. No. 5,198, 203), MCM-49 (U.S. Pat. No. 5,236,575), MCM-56 (U.S. Pat. No. 5,362,697), ALPO-I I (U.S. Pat. No. 4,310,440), titanium aluminosilicates (TASO), TASO-45 (European Patent Application No. EP-A-O 229 295), boron silicates (U.S. Pat. No. 4,254,297), titanium aluminophosphates (TAPO) (U.S. Pat. No. 4,500,651), mixtures of ZSM-5 and ZSM-I I (U.S. Pat. No. 4,229,424), ECR-18 (U.S. Pat. No. 5,278, 345), SAPO-34 bound ALPO-5 (U.S. Pat. No. 5,972,203), International Publication No. WO 98/57743 published Dec. 23, 1988 (molecular sieve and Fischer-Tropsch), U.S. Pat. No. 6,300,535 (MFI-bound zeolites), and mesoporous molecular sieves (U.S. Pat. Nos. 6,284,696, 5,098,684, 5,102,643, and 5,108,725), which are all herein fully incorporated by reference.

As regards to the size of crystals of molecular sieve, it is not bigger than 50 nm, preferably it is not bigger than 40 nm, most preferably not bigger than 30 nm, even more preferably it is in the range of 15 nm or not bigger than 15 m. Such small crystals size cannot be evidenced by X ray diffraction, because the crystals are too small. It is believed that the crystals have a size which is below the detection limit of the X ray diffraction technique. The detection limit of XRD being in the range of 50 nm, it is believed that the crystals are smaller than 50 nm. Therefore the catalyst composition of the present invention does not present the characteristic X ray bands of the molecular sieve. However, the presence of such crystals can be evidenced by indirect technique. In particular, the presence of such crystal can be evidenced by an increase of the surface area with a small increase of the microporous volume. It can also be evidenced by the presence of the characteristic NMR $^{13}C$ signal of the template inside such crystal if template is present during the synthesis. It can also be evidenced by the presence by increase the acidity and detection of the acid sites by FTIR of adsorbed Pyridine. Finally, it can be evidenced by the presence of tetrahedrally coordinated Al via $^{27}Al$ MAS NMR.

On the other hand, the minimum size reachable while maintaining a crystallographic structure is the size of a crystal unit cell. Considering the crystallographic structure of an unit cell, it is possible to estimate the minimum size. In the case of FAU, a minimum size to form tetrahedrally coordinated Al was estimated at around 15 nm to have at least one unit cell. Consequently it is foreseen that the minimum reachable size of a molecular sieve is in the range of 15 nm or from 15 nm to at most 50 nm.

When it is referred to the "average size" of the crystal of molecular sieves, it shall be interpreted as referring the maximum diameter of the particle. Indeed the particles of molecular sieve are not necessarily spherical; therefore the term size refers to their biggest length. As all the particles do not have exactly the same size, the term "average" shall refers the position of the maximum of a Gaussian curve obtained while counting the particles as a function of their size. When the particles are deposited on the inorganic porous material, they maintain their size. However when the number of particle increases, they may at least partially agglomerate to form a coating. In this case, the average particle size merely relates to the thickness of the coating which should stay below 50 nm to avoid having a XRD pattern. Indeed the length of the coating might be higher than 50 nm as long as the thickness stays below 50 nm and does not lead to an XRD signature.

Detailed Description of the Process of Preparation of the Catalyst Compositions

The method of preparation described in this part is to be used to prepare the catalyst composition described in the above part. All embodiments of the catalyst composition described in the above part are linked and should be considered in combination with all the embodiments of the method of preparation and all its related embodiments described in this part.

The process of preparation include the following steps:

a) providing an inorganic porous material;

An inorganic porous material is used as a carrier for the crystal of molecular sieves. It presents at least a mesoporosity, i.e. pores of at least 2 nm. Advantageously the inorganic porous material presents a macroporosity, i.e. pores of at least 50 nm. Preferably the pore diameters of the carrier are of at least 100 nm, more preferably of at least 200 nm. The large diameter of the pores allows giving additional accessible surface area inside the carrier itself for receiving crystals of molecular sieves.

The carriers used in the prior art are small particles of material having no mesoporosity. In this case, the inside of the particles of carrier cannot be used for catalyzing the reaction. On the contrary, an inorganic porous material is used in the invention to disperse the crystals of molecular sieve. Using a porous material allows increasing the surface available for dispersing the crystals of molecular sieve and therefore it allows increasing the overall activity of the catalyst composition.

In addition, dispersing the crystals of molecular sieve on porous material allows stabilizing the crystals. Indeed, crystals of molecular sieve having a diameter of less than 50 nm are not stable and have the tendency to agglomerate when performing catalyst reactions. The catalyst compositions according to the invention allow stabilizing the small size crystals by fixing them on the surface of a carrier.

The porous material is preferably amorphous and it presents porosity with pore diameters of at least 2 nm (either a macroporosity or a mesoporosity). It shall contain Al2O3 and SiO2 with an atomic ratio Al/Si>1. It may be inert or not for the reaction in which the catalyst composition is used. Preferably the material has some acid sites, which could be measured, for instance, by TPD NH3. When the porous material is amorphous, the catalyst compositions exhibit no detectable crystallinity by X ray diffraction. As an alternative, the porous material is crystalline and the catalyst compositions exhibit an X ray pattern identical to the X ray pattern of the said crystalline porous material.

In an embodiment, the porous material is an inorganic material selected from alumina doped with silica, metal aluminosilicates, mixed metal oxides, or gels including mixtures of silica, alumina and metal oxides, amorphous, or amorphous silica aluminophosphates.

In addition to silicon and aluminum, the porous material may contain O, Na, Ca, Mg, Li, La, Ti, Zr, P, As, Be, B, Cr, Co, Ga, Ge, Fe, Ni, Mo, W, Ag, Sn, Mn, S, C or Zn.

If the porous material is amorphous, it contains a silica alumina, and more preferably the porous material is a high purity silica alumina material. High purity means that the content of impurities (elements different from Si, O, Al) is below 500 ppm weight.

In preferred embodiment the porous materials has a very low S, Cl, Br, F, I content below 100 ppm weight.

In preferred embodiment the precursors of porous materials has a been obtained by alkoxide route or by using the alumina precursors obtained by alkoxide route.

In preferred embodiment the porous materials have a pore volume of at least 0.25 $cm^3/g$ measured using ASTM D4365.

b) optionally calcinating said porous material at temperature from 400° C. to 1200° C.;

Calcination consists in the treatment of a solid at elevated temperature i.e. at least 400° C. in an oven without gas circulation or under air flow, oxygen flow or N2 flow. This first optional calcination considered in the preparation of the catalyst composition is used to stabilize the porous material. By stabilization, it should be understood that this calcination allows improving surface stability during the contact with a solution containing precursors for the molecular sieve f). One person skilled in the art understands the effect of calcinations via limiting the further dissolution of the elements constituting the material. As a matter of example, the calcination is used in the first step to limit the dissolution of the aluminium during the further steps, when the porous material is put in contact with the solution containing the surface modifying agent or the precursors of molecular sieves.

providing a solution containing at least one charger surface modifying agent;

The charge surface modifying agent can consist of any type of component allowing modification of the charge surface of the porous material. Without willing to be bound to any theory, it is believed that during the crystallisation of a molecular sieve, very small crystals are formed. Those small size crystals are electrically charged and those charges are compensated by counter ions present in the solution. Because of those charges, the small size crystals cannot easily be deposited directly on the inorganic porous support. It has been discovered that impregnation of the inorganic porous material with charge surface modifying agent prior to deposition of the small size crystals allows depositing those small size crystals on the porous surface with a good dispersion. It is believed that during the maturation step, the charge modifying agent deposited on the inorganic porous material surface eases deposition of the small size particles on the porous material surface by limiting the electrostatic repulsion between the small size crystals and the surface of the porous material.

Such components can be organic or inorganic. Organic charge modifying agent are generally water-soluble polymers which can either be non ionic or ionic. Ionic polymer can be of anionic, cationic or amphoteric types.

As a non limiting example of inorganic charge modifying agent, one can cite aluminium, aluminium chloride and derivative components such as poly aluminium chloride or sodium silicate (activated silica). Advantageously the inorganic compounds used are the same as the compounds used to prepare the solution containing the source of the elements for the molecular sieve.

In another embodiment, charge surface modifying agents are organic molecule having a charge compensated with a counter anion. Water soluble polymers having surfactant properties (ionic or non ionic surfactant), anionic polymers, cationic polymers or polymers used in flocculation process are preferred. As a non limiting example, any polymer from the family of poly diallyl dimethyl ammonium chloride (PDDA) could be used. Additionally other polymers such as polyacrylamide [9003-05-8]; poly(ethylene oxide) [25322-68-3]; poly(sodium acrylate) [9003-04-7]; poly[2-(N,N,N-trimethylamino)ethyl acrylate] (chloride salt) [54076-97-0]; polyethylenimine [26913-06-4]; poly[N-(dimethylaminomethyl)acrylamide] [25765-48-4]. Other nonionic homopolymers from 1-vinyl-2-pyrrolidone[88-12-0], N-vinylformamide [13162-05-5], methoxyethylene [107-25-5], etc. Poly(vinyl alcohol) [9002-89-5] is synthesized by hydrolysis of poly(vinyl acetate). Very high molecular mass poly(ethylene oxide) [25322-68-3] is obtained by polymerizing ethylene oxide over special catalysts, e.g., alkaline-earth carbonates or aluminium alcoholates (C1-C4).

As non limiting example, ionic charge modifying agents are copolymers derived from acrylamide [79-06-1] and a charged comonomer. Anionic polymers are synthesized as homopolymers or acrylamide copolymers of the alkali-metal or ammonium salts of acrylic acid [79-10-7]. Methacrylic acid [79-41-4], maleic acid [6915-18-0], ethylenesulfonic acid [1184-84-4], 4-styrenesulfonic acid [98-70-4], and 2-methyl-2-[(1-oxo-2-propenyl)amino]-1-propanesulfonic acid [15214-89-8] can also be used as comonomers in acrylamide copolymers. Other water-soluble cationic polymers can be used for the production of cationic polymers for instance: substituted acrylamide and methacrylamide salts [16-19]; N-vinylformamide [13162-05-5] and N-vinylacetamide [5202-78-8], which are polymerized and hydrolyzed in alkaline or acidic media to "vinylamine" copolymers [593-67-9] [20-23]; and salts of N-vinylimidazole [1072-63-5], 2-vinylpyridine [100-69-6] or 4-vinylpyridine [100-43-6].

Efficiency of the modification of the charge surface of the mesoporous material can easily be checked via zeta potential measurement of the material obtained at step d). A comprehensive list of component having the ability to neutralize the charge surface can be found in *Ullmann's Encyclopaedia of Industrial Chemistry, 6$^{th}$ completely revised edition*, volume 14 pages 201-212 incorporated therein by reference.

d) putting in contact the solution of step c) and the material obtained at step b to obtain a material modified with a charge surface modifying agent;

Putting in contact the solution and the material can consist in any of the usual impregnation technique used to prepare catalyst compositions. For instance, it can consist in wetness impregnation technique in which the solid is put in contact with the exact amount of solution filling its porosity. It can consist in equilibration impregnation technique in which the solid is put in contact with a large excess of solution. Then the solid may either be separated via filtration or the excess of liquid may be evaporated. In one embodiment, the impregnation can be performed at room temperature. In another embodiment, impregnation can be performed at temperature ranging from room temperature up to 150° C.

Optimization of the impregnation step is known in the art. In the case of the impregnation of the charge surface modifying agent, the good dispersion of this agent on the surface of the porous support can be checked with measurement of the charge surface of the porous material. In particular, the zeta potential of the porous material can be monitored. Further reference and details about the zeta potential can be found in *Ullmann's Encyclopaedia of Industrial Chemistry, 6$^{th}$ edition*, volume 11, page 702-703 incorporated therein by reference.

e) providing a solution containing precursors for the molecular sieve;

The solution containing precursors of molecular sieve or seeds of molecular sieve consists in the elements in any form provided they are soluble in the solution and provided they can be used to prepare the corresponding molecular sieve. In a preferred embodiment, preparation of the solution containing molecular sieve precursors comprise the mixing of an appropriate quantities of sodium silicate, sodium aluminate, sodium hydroxide and, optionally, a organic template. In a most preferred embodiment, the mixing is performed in a controlled manner and heating the resulting mixture for a time sufficient for the seeds to mature but insufficient for cloudiness to occur.

In an embodiment, the sources of the various elements of the metallosilicate may be any of those found in the commerce or prepared on purpose. For example, the source of silicon may be a silicate, e.g., a tetraalkyl orthosilicate, precipitated or pyrogenic (fumed) silica, or preferably an aqueous colloidal suspension of silica.

Preferably, the inorganic source of silicon has a limited solubility in the water before addition of alkali medium.

When the metallosilicate is an aluminosilicate zeolite, the source of aluminum is preferably hydrated alumina dissolved in an alkaline solution or aluminum metal, a water-soluble aluminum salt, e.g., aluminum sulphate or aluminium chloride, sodium-aluminate or an alkoxide, e.g., aluminum isopropoxide. When the metallosilicate is a borosilicate zeolite, the source of boron is preferably hydrated boron oxide dissolved in an alkaline solution or a water-soluble boron salt, e.g., boron chloride or an alkoxide. When the metallosilicate is a ferrosilicate or gallosilicate, the source of iron or gallium can almost be any iron or gallium salts that are readily soluble in water. When the metallosilicate is titanosilicate, the source of titanium can be titanium halides, titanium oxyhalides, titanium sulphates or titanium alkoxides. The atomic ratio of silicon to metal depends on the metal and on the use of the metallosilicate and is at least 2/1 to about 10000/1, preferably from 5/1 to about 5000/1 and most preferred from about 10/1 to 1000/1.

In another embodiment, the molecular sieve is preferably obtained without direct addition of template according to a method known from the man skilled in the art. Optionally one or more templating agent (or directing agent), such as organic or inorganic compounds containing nitrogen, oxygen, sulfur, or phosphorous may be introduced into the synthesis mixture. When the directing agent is a cation, it may also be introduced in the form of a mixture of hydroxide and salt, e.g., a halide. The agent used will depend on the metallosilicate prepared by the process. The amount of the directing agent depends on the metallosilicate prepared by the process. The source of M cations may be alkali or alkaline earth hydroxides or salts. M may also be ammonium hydroxide or salts. Together with the directing agent(s) the M cation will impact the pH of the crystallising medium The order of mixing of the precursors of metal and silicon is not essential and will depend on the molecular sieve being prepared. Optionally the crystallization medium may be aged at a temperature at which no crystallization occurs, optionally nucleation may be started. The person skilled in the art knows equipment used to prepare crystals of molecular sieves of the type used in the present invention. Generally, metallosilicates can be prepared by using autoclaves, which have sufficient agitation to homogenize the crystallization mixture during heat up until the effective nucleation and crystallization temperature of the mixture is achieved. The crystallization vessel can be made of a metal or metal alloys resisting the conditions of the crystallization or optionally can be coated with a fluorocarbon such as Teflono0 ™. Other means of introducing agitation known to one skilled in the art can be employed, such as pumping the synthesis mixture from one part of the autoclave to another.

In a preferred embodiment the solution containing precursor for the molecular sieve of step e) contains small crystals of molecular sieves and is XRD amorphous i.e. exhibit not detectable crystallinity by X ray diffraction.

f) reacting molecular sieves by:
   i) maturating during a period of time from 0 to 50 h the solution of step
   e) in order to obtain crystal of molecular sieve with a maximum size of 50 nm preferably 10 nm, measured by DLS and subjecting a modified porous material in a contact with the maturated solution under appropriate conditions to form the molecular sieve crystals on the surface of the modified porous material obtained at step d); and/or
   ii) putting in contact said modified porous material obtained at step d) with the solution of step e) and maturating during a period of time from 0 to 50 h the obtained mixture under conditions to increase the acidity of the catalyst composition without modifying its X ray diffraction pattern and/or to form the crystals of molecular sieve;

The maturation consists in the treatment of the mixture constituted of porous material with the solution containing the precursor of crystal molecular sieve. This step is performed to allow deposition and/or crystallisation of the crystal of molecular sieve on the porous material. In one embodiment, the solution containing the precursor of crystal molecular sieve is firstly maturated to initiate crystallisation of the molecular sieve (step f) i)). In another embodiment, the solution is put in contact with the porous material impregnated with a charge modifying agent without being firstly maturated. In this last case, the crystallisation is started directly on the porous material (step f) ii)). In still another embodiment, the solution is firstly maturated, then put in contact with the porous material impregnated with a charge modifying agent and the mixture obtained is finally maturated.

Without willing to be bound to any theory, it is believe that the maturation of step f) ii) consists either in usual crystallisation step as known per se in the art or a deposition step in which the small size crystals of molecular sieve already present in the solution are deposited on the porous material.

The maturation steps can last from 10 min up to 48 h, more preferably it lasts from 1 h to 24 h, even more preferably it lasts from 2 h to 12 h.

In another embodiment, maturation is optional.

Putting in contact the solution with the solid at step f) i) or f) ii) is performed in a similar way as in step d).

g) separating the solid from the liquid if any of the mixture obtained after step f);

Separation of the solid from the liquid can be performed by any means known in the art, for example, one can cite filtration, drying at least at 100° C., nano filtration etc.

h) calcinating, the solid obtained at step g).

The calcination performed in the step h) is performed to remove the organic compounds present on the solid via their combustion under $O_2$ or air or any oxidizing atmosphere. It can also consist in removing the impurities (i.e. components other than organic components, for instance counter ions) that may be present on the surface. The calcinations is performed at a temperature of at least 400° C. Calcination is preferably performed in a temperature range of 400° C. to 1200° C.

Other Comments on the Process

This process allows preparing a catalyst composition with small size crystals of molecular sieve dispersed on its surface.

In an embodiment, the preparation of the catalyst composition described leads to a porous material on which were deposited crystals of molecular sieve having an average diameter not bigger than 50 nm, preferably not bigger 40 nm, more preferably not bigger than 30 nm, even more preferably in the range of about 15 nm or below.

In another embodiment, the steps e) to g) are repeated at least two times in order to increase the content of crystals of molecular sieve deposited on the porous materials.

In another embodiment, the catalyst compositions could be further modified by metal deposition, phosphorous deposition, steaming, ion-exchange, acid leaching, alumination, silication, surface functialization by grafting etc.

The acid leaching can be made with an organic acid such as citric acid, formic acid, oxalic acid, tartaric acid, malonic acid, succinic acid, glutaric acid, adipic acid, maleic acid, phthalic acid, isophthalic acid, fumaric acid, nitrilotriacetic acid, hydroxyethylenediaminetriacetic acid, ethylenediaminetetracetic acid, trichloroacetic acid trifluoroacetic acid or a salt of such an acid (e.g. the sodium salt) or a mixture of two or more of such acids or salts. The other inorganic acids may comprise an inorganic acid such as nitric acid, hydrochloric acid, methansulfuric acid, phosphoric acid, phosphonic acid, sulfuric acid or a salt of such an acid (e.g. the sodium or ammonium salts) or a mixture of two or more of such acids or salts.

In another embodiment, the process of preparation of catalyst compositions according to the invention may include one or more of the following steps, said steps being performed after step h) in any order:

introduction of phosphorous by impregnation of the catalyst composition by a solution containing phosphorous, said step being optionally followed by further steps of calcinations and/or steaming;

addition of at least one metal selected from the group: B, Cr, Co, Ga, Fe, Li, Mg, Ca, Mn, La, Ti, Mo, W, Ni, Ag, Sn or Zn, Pt, Pd, Ru, Re, Os, Au or any combination thereof, by impregnation of the catalyst compositions by a solution containing the selected metals salts;

addition of at least one binder selected from silica, silica alumina, metal silicates, metal oxides such as $ZrO2$ and/or metals, amorphous alumophophate or silica alumophosphates, gels including mixtures of silica and metal oxides, amorphous alumophophate or any combination thereof, by spray drying, extrusion or any suitable method known to the man skilled in the art;

shaping of the catalyst composition by extrusion.

Binder materials are typically effective in reducing overall catalyst cost, acting as thermal sinks assisting in shielding heat from the catalyst composition for example during regeneration, densifying the catalyst composition, increasing catalyst strength such as crush strength and attrition resistance, and controlling the rate of conversion in a particular process. The binder could be the same or different from the initial porous materials. The binder is an inorganic material selected from silica, metal silicates, metal oxides such as ZrO2 and/or metals, or gels including mixtures of silica and metal oxides. It is desirable to provide a catalyst having good crush strength. This is because in commercial use, it is desirable to prevent the catalyst from breaking down into powder-like materials. Such oxide binders have been employed normally only for the purpose of improving the crush strength of the catalyst. A particularly preferred binder for the catalyst of the present invention comprises silica, alumina, amorphous alumophophate, silica alumophosphates or silica alumina. The relative proportions of the finely divided crystalline silicate material and the inorganic oxide matrix of the binder can vary widely.

Detailed Description of the Possible Use of the Catalyst Compositions

As regards to the use of the catalyst, it can be used as catalyst in any reaction requiring acidic active sites. It can also be used as a support where acidic properties for the support are required. It can also be used as a co-catalyst with another catalyst, for instance in a mechanical mixture or a constituent of the formulation; it can be added before formulating or as a part of the formulation. For instance, it may be used as a catalyst in the reaction of FCC or a catalyst additive for the FCC reaction.

The materials disclosed in the invention may be also useful as an adsorbent or a support for the adsorbent for different applications.

Because the catalyst composition is characterized by a uniform spatial distribution of the crystals molecular sieve in the porous material this results in the presence of catalytic active sites well dispersed (evidenced by SEM) in the porous material. The catalyst composition of the present invention by itself or in combination with one or more catalytically active substances can have high activity, high selectivity, high stability, or combinations thereof when used as catalysts for a variety of hydrocarbon conversion processes.

The catalyst composition (as such or after modification with metals or metal oxides: Ga, Zn, Fe, Mo, Ni, Co) can be used for reaction like catalytic pyrolysis of hydrocarbonaceous material originated from biomass or different types of garbage to produce fuel, aromatics or olefins. Catalytic upgrading by pyrolysis vapors using the catalyst composition is a promising method for removing oxygen from organic compounds and converting them to hydrocarbons.

In a particular embodiment the catalytic pyrolysis with the catalyst composition is performed as a co-processing of the bio-feedstock containing oxygen with the fossil feedstocks. For example, the said co-processing is performed in the FCC unit.

Hydrocarbonaceous material useful as a feedstock for the invention may comprise, for example, a component such as xylitol, glucose (e.g., α-D-glucose, β-D-glucose), cellobiose, cellulose, hemi-cellulose, lignin, sugar cane bagasse, glucose, wood, and corn stover together with pyrolysis products thereof and combinations of such components and/or their pyrolysis products.

Other examples of hydrocarbonaceous materials include, for example, plastic waste, recycled plastics, agricultural and municipal solid waste, food waste, animal waste, carbohydrates, lignocellulosic materials (e.g., wood chips or shavings, lignocellulosic biomass, etc.), or combinations thereof, among others.

As used herein, the term "biomass" is given its conventional meaning in the art and is used to refer to any organic source of energy or chemicals that is renewable. Its major components can be (1) trees (wood) and all other vegetation; (2) agricultural products and wastes (corn, fruit, garbage ensilage, etc.); (3) algae and other marine plants; (4) metabolic wastes (manure, sewage); and (5) cellulosic urban waste.

The embodiments described herein also involve chemical process designs used to perform catalytic pyrolysis. In some cases, the processes may involve the use of one or more fluidized bed reactors (e.g., a circulating fluidized bed reactor, turbulent fluidized bed reactor, bubbling fluidized bed reactor, etc.), or batch reactors including circulating flow batch reactors (slurry reactor).

The process may involve, in some embodiments, pyrolyzing within a reactor (e.g., a fluidized bed reactor) at least a portion of a hydrocarbonaceous material under reaction conditions sufficient to produce one or more pyrolysis products. In addition, the process may involve catalytically reacting at least a portion of the one or more pyrolysis products using a catalyst under reaction conditions sufficient to produce one or more fluid hydrocarbon products. In some embodiments, one or more fluid hydrocarbon products may be produced from said pyrolysis products by dehydration, decarbonylation, decarboxylation, isomerization, oligomerization, and dehydrogenation reactions. The pyrolysis and catalytic reaction processes may occur, in some cases, in a single reactor. The chemical processes may be used, in some cases, for specific fluid hydrocarbon product production (e.g., aromatics and/or olefins). In some cases, a portion of the olefins produced by the chemical process may be recycled into the feed stream via which the hydrocarbonaceous material is fed to the reactor (e.g., the pyrolysis reactor).

A process of hydrocracking of extra heavy oil capable of obtaining cracked light oil with higher yields. The process could be performed in fixed, fluidized, batch or slurry reactor. In the preceding process, reaction conditions in the reaction step are a reaction pressure of 25-300 Atm; a reaction temperature of 300-500° C.

Characterization Techniques

As regards to the surface area and porous volume measurements, it is measured via N2 adsorption using usual surface area measurements. In particular, surface area measurements such as "BET" measurement can be used (i.e. ASTM D3663 for the surface area and D4365 for the porous volume). Other techniques well known in the art can also be considered such as mercury adsorption techniques (ASTM D4284). All measurements and data plots as utilized herein were made with a Micromeritics® Tristar 3000® analyzer.

As regards to the acidity measurement, it is measured by:

Pyridine adsorption quantified via Infra Red measurements. IR spectra were recorded on Nicolet Magna 550 FT-IR spectrometer with 4 $cm^{-1}$ optical resolution, with one level of zero-filling for the Fourier transform. Prior to the measurements, the catalysts were pressed in self-supporting discs (diameter: 1.6 cm, 10 mg $cm^2$) and activated in the IR cell (attached to a vacuum line) at 723° K for 4 h up to 106 Torr (14132.17 Pa). The IR cell was equipped with KBr windows, which enabled to register spectra in the spectral region down to 400 $cm^{-1}$. The pressure of the adsorbed gases was measured by two Barocel gauges, the one was attached directly to the sample containing compartment of the cell. Another one enabled us to measure a dose of gas in the known volume before adsorption it into the cell. The sample temperature during the treatment or recording of spectra was monitored by a chromel-alumel thermocouple inserted into the heater or into the coolant compartment of the cell. Adsorption of pyridines: pyridine (Py) was performed at 423° K. The excess of probe molecules was further evacuated at 423° K. The adsorption-evacuation was repeated several times until no changes in the spectra were observed. The amount of the adsorbed Py was measured by means of extinction coefficient $\varepsilon_{1545}$ (B-pyridine)=1.8 cm μmol$^{-1}$ and $\varepsilon_{1455}$ (L-pyridine)=1.5 cm μmol$^{-1}$. The pyridine adsorption allowed quantifying the Bronsted and Lewis acidic sites.

TPD ammonia measurement (TPD NH3), it is performed on a fully automated AutoChem II (Micromeritics) equipped with a TCD detector (but not equipped with an IR spectrometer). A Pyrex®™ cell with approximately 0.4 g of sample to be characterized is placed in an oven and the following steps are performed:

Activation: this step is performed under a flow rate of He of 50 cm3/min. The temperature is increased from room temperature up to 600° C. with a temperature increase of 20° C./min. The temperature is then maintained at 600° C. during 1 h. The temperature is then decreased at 100° C. with a cooling speed of 10° C./min.

Saturation: this step is performed at 100° C. During a first hour, the solid is put in contact with a flow of 30 cm3/min of a mixture of 10 weight % of NH3 diluted in He. Then during the next 2 h, the solid is put in contact with a flow rate of 50 cm3/min of He.

Analysis: this step is performed under a flow of 50 cm3/min of He. The temperature is increased at 600° C. with a temperature increase of 10° C./min. Once the temperature of 600° C. has been reached, this temperature is maintained for 1 h. The cell is then cooled down and weighted. The amount of NH$_3$ deposited on the solid is determined as μmol NH$_3$ desorbed in the temperature range from 100° C. to 600° C. from the sample normalized by a weight of the sample taken after the measurement.

TPD ammonia measurements can be used to quantify the Bronsted and Lewis acidic sites. However, to do so, it is necessary to follow the IR spectra of the NH3 adsorbed on the solid. In our case, the TPD measurement unit was not equipped with an IR spectrometer. The quantification of the Bronsted and Lewis sites was performed via pyridine adsorption measurements.

As regards to the X ray diffraction measurements, powder X-ray diffraction (XRD) patterns were obtained with a PANalytical X'Pert Pro diffractometer using Cu Kα radiation (λ=1.5418 Å, 45 kV, 40 mA). All analyses were performed using ca. 20 mg powder loaded on a silicon wafer. The samples were studied in the 5-50° 2θ range with a scanning step of 0.0167° s$^{-1}$.

As regards to the measurement of the crystal amount, the $^{13}$C MAS NMR measurements were obtained using a Bruker spectrometer using the following conditions: $^{13}$C-$^{1}$H cross polarization, $^{13}$C (100.6 MHz), $^{1}$H (400.3 MHz); Rotation speed=12.5 kHz. Number of scans=30 k; Spectra were normalized to 30 k scans and 20 mg sample.

As regards to the catalytic tests, catalytic cracking of 1,3,5-tri-isopropyl-benzene (TiPBz) was carried with conventional atmospheric flow reactor. 20 mg of catalyst were loaded at the center of a stainless steel tubular reactor (internal diameter of 12.7 mm i.e. ½ inches) and activated in-situ at 460° C. (ramping from room temperature at 5° C./min) under air flow (50 ml/min) for 1 h and under N2 flow (50 ml/min) for 0.5 h. The partial pressure of TiPBz (Alfa Aesar ca. 97%) was set at 170 Pa in a saturator held at 70° C. Weight hour space velocity (WHSV) was held constant at 8 h$^{-1}$ for all tests. The catalyst activity was evaluated at 300° C. by exposing them to the feed for 180 min. The reaction products, transferred via a line heated at 150° C. to a gas sampling valve, were monitored online by a Gas chromatograph equipped with a FID detector.

As regards to the content of molecular sieve deposited on the porous material, it is determined based on the weight loss of organic template via thermogravimetric analysis (TG-DTA). Once prepared, the catalyst compositions are firstly exchanged with Na+ in order to eliminate loosely attached template molecules. Once exchanged, they are analyzed via thermogravimetry. The weight loss corresponding to the template located inside the molecular sieve is identified by comparison with the thermogravimetric analysis obtained with the corresponding molecular sieve impregnated with the same template. The concentration of molecular sieve is obtained by subtracting from the weight loss obtained with the catalyst composition, the weight loss obtained with the porous material impregnated with the same template and exchanged with Na+ to remove loosely attached template.

As regards to the thermogravimetric analysis (TG-DTA), it is performed from 30° C. to 600° C. at a ramp rate of 5° K/min under 40 mL/min air flow, followed by a plateau at 600° C. for 10 min. The amount of active phase grown on carrier is determined based on the weight loss of organic templates in the temperature range of 350-500° C. The actual weight loss was obtained by subtraction of the amount adsorbed on the reference sample (i.e. the carrier without deposition of crystal of molecular sieves).

As regards to the Dynamic Light Scattering (DLS) measurements, it is performed on a Malvern Zetasizer Nano Series DLS instrument. The samples were diluted in excess distilled water in a test cell and all measurements were performed at 25° C. for 30-180 s.

As regards to the solid state MAS NMR, it is performed on a Bruker DRX500 spectrometer ($^{27}$Al at 132.32 MHz, Pulse 0.1 μsec (pi/100), relaxation delay 0.5 sec). Before the measurements, the samples were saturated at room temperature and atmosphere pressure in desiccators for 24 h with the vapor of an aqueous solution of KCl. $^{27}$Al MAS NMR measurements were performed using a probe 4 mm. Chemical shifts were referenced to a 0.1 M AlCl3 solution (0 ppm). Rotors were spun at 14.5 kHz. At least 256 scans depending on Al concentration were acquired for each spectrum.

DESCRIPTION OF THE FIGURES

FIG. 1 presents the DRX patterns of the porous material prepared according to example 1.

Figure 2:
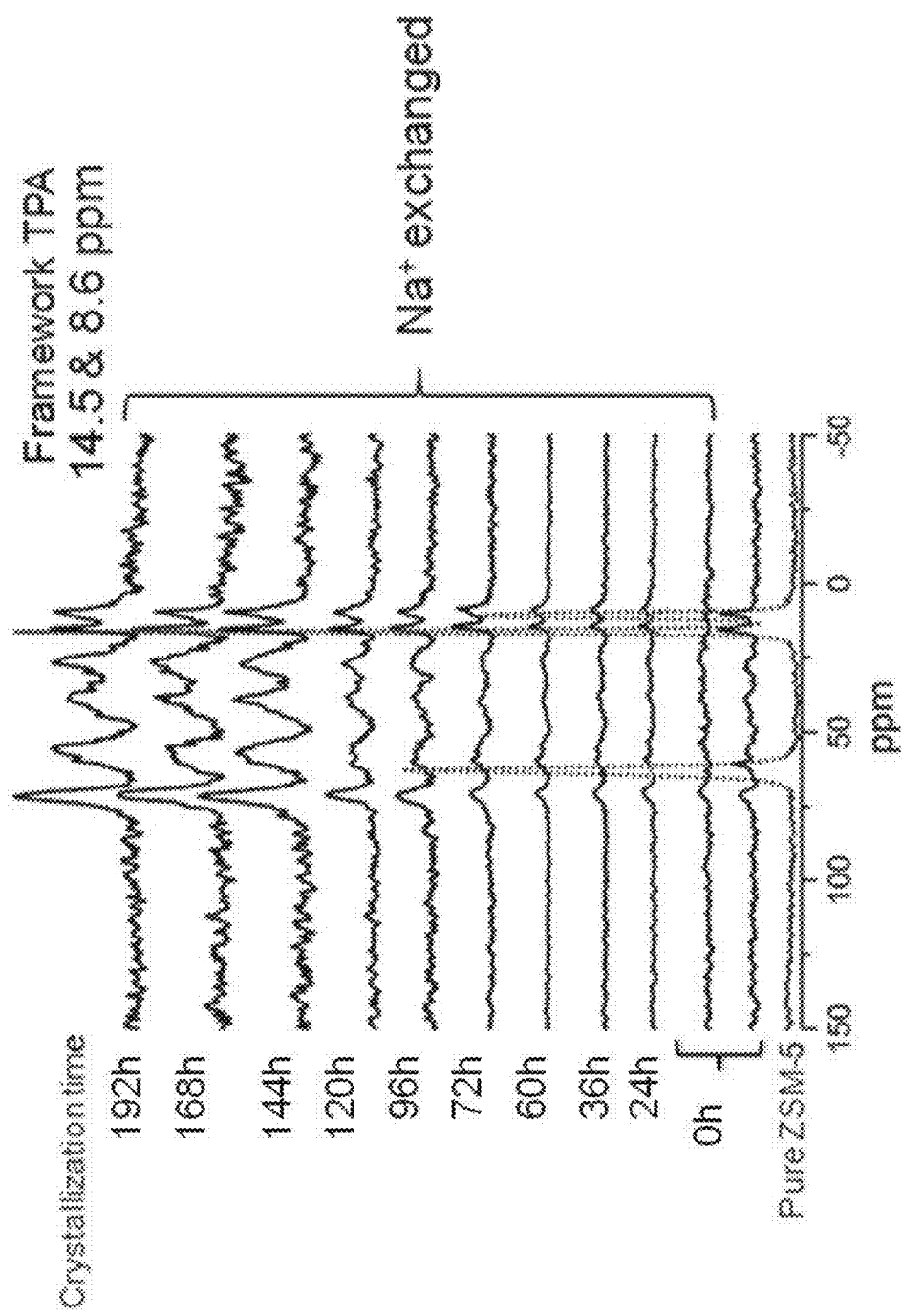
FIG. 2 presents NMR $^{13}C$ spectra of the catalyst composition according to example 1.

FIG. 2 presents NMR $^{13}$C spectra of the catalyst composition according to example 1.

Figure 3:
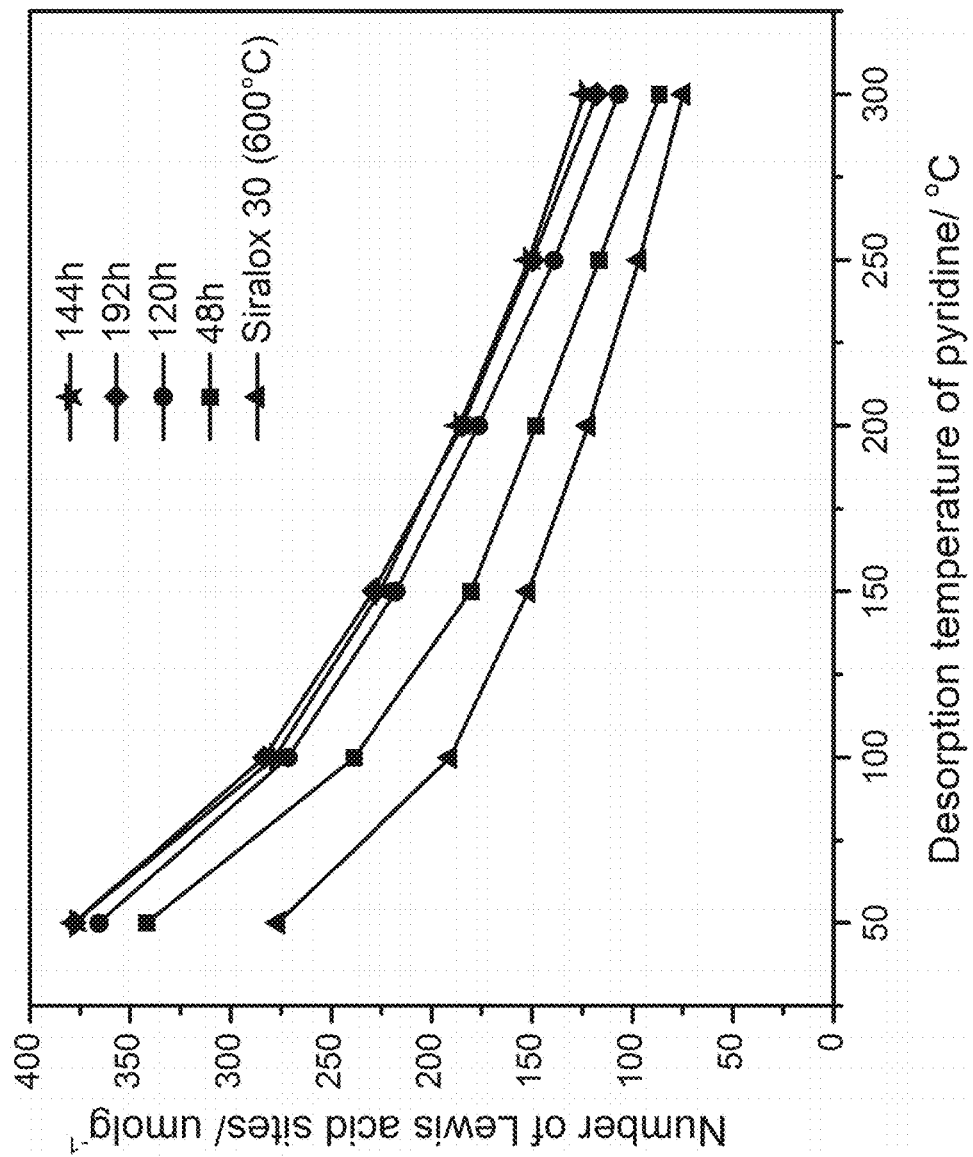
FIG. 3 presents the measures of pyridine adsorption of the catalyst compositions prepared according to example 1.

FIG. 3 presents the measures of pyridine adsorption of the catalyst compositions prepared according to example 1

Figure 4:
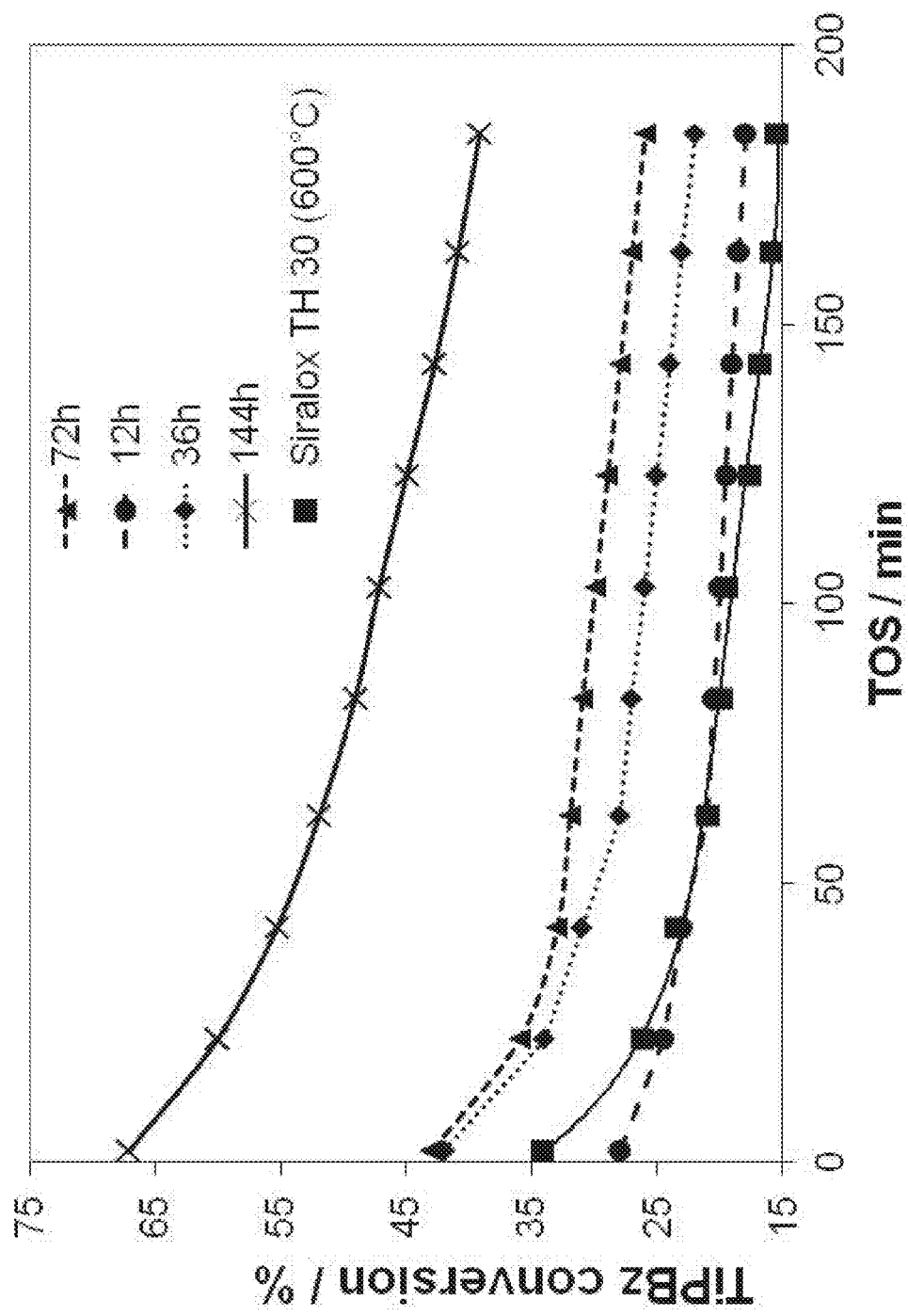
FIG. 4 presents the catalytic tests of the solids prepared according to example 1.

FIG. 4 presents the catalytic tests of the solids prepared according to example 1

Figure 5:
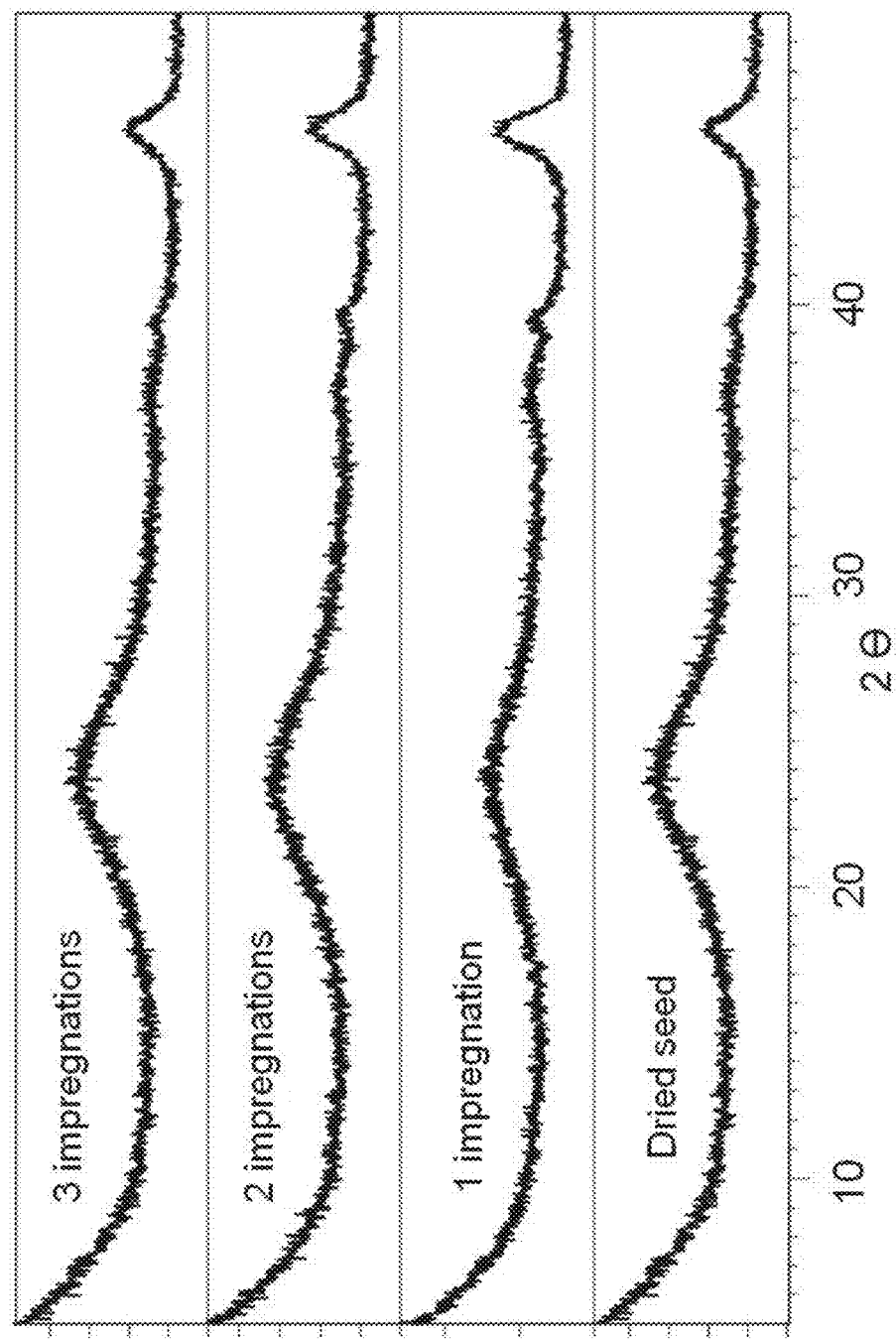
FIG. 5 presents the DRX patterns of the materials prepared according to example 4.

FIG. 5 presents the DRX patterns of the materials prepared according to example 4.

Figure 6:
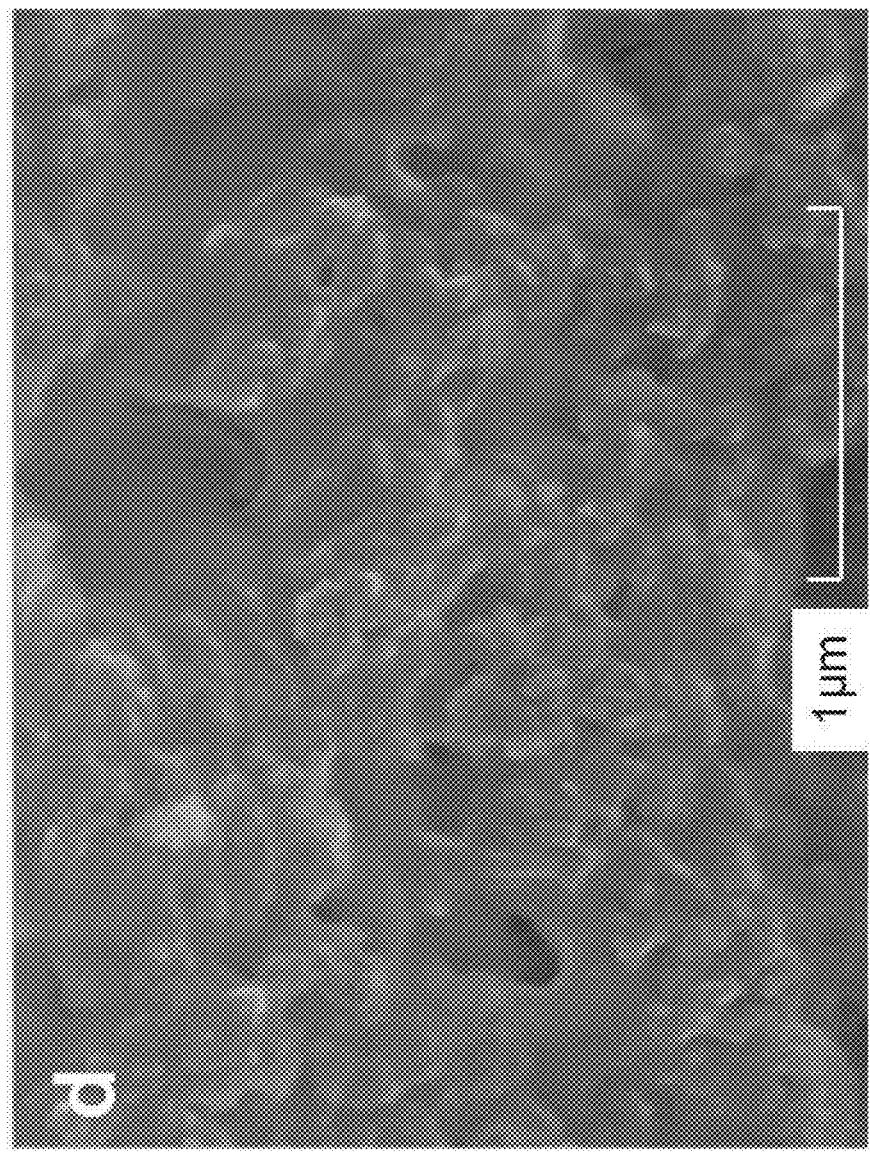
FIG. 6 presents the SEM micrographs of the materials prepared according to example 4 after three impregnations of the molecular sieve precursor on the porous material (sample "3 impregnations").

FIG. 6 presents the SEM micrographs of the materials prepared according to example 4 after three impregnations of the molecular sieve precursor on the porous material (sample "3 impregnations").

Figure 7:
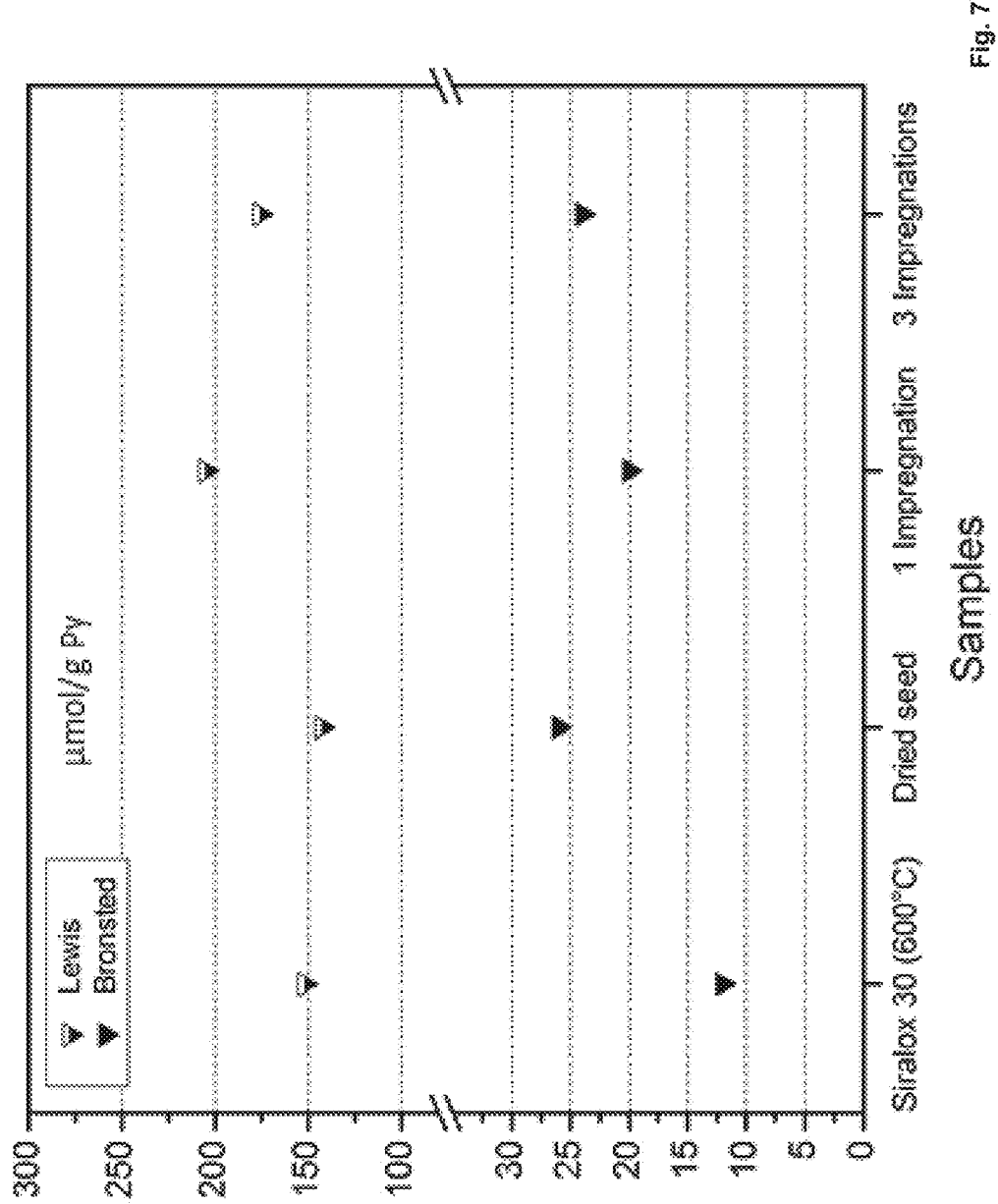
FIG. 7 presents the acidic sites quantification measured using pyridine adsorption according to example 4.

FIG. 7 presents the acidic sites quantification measured using pyridine adsorption according to example 4.

Figure 8:
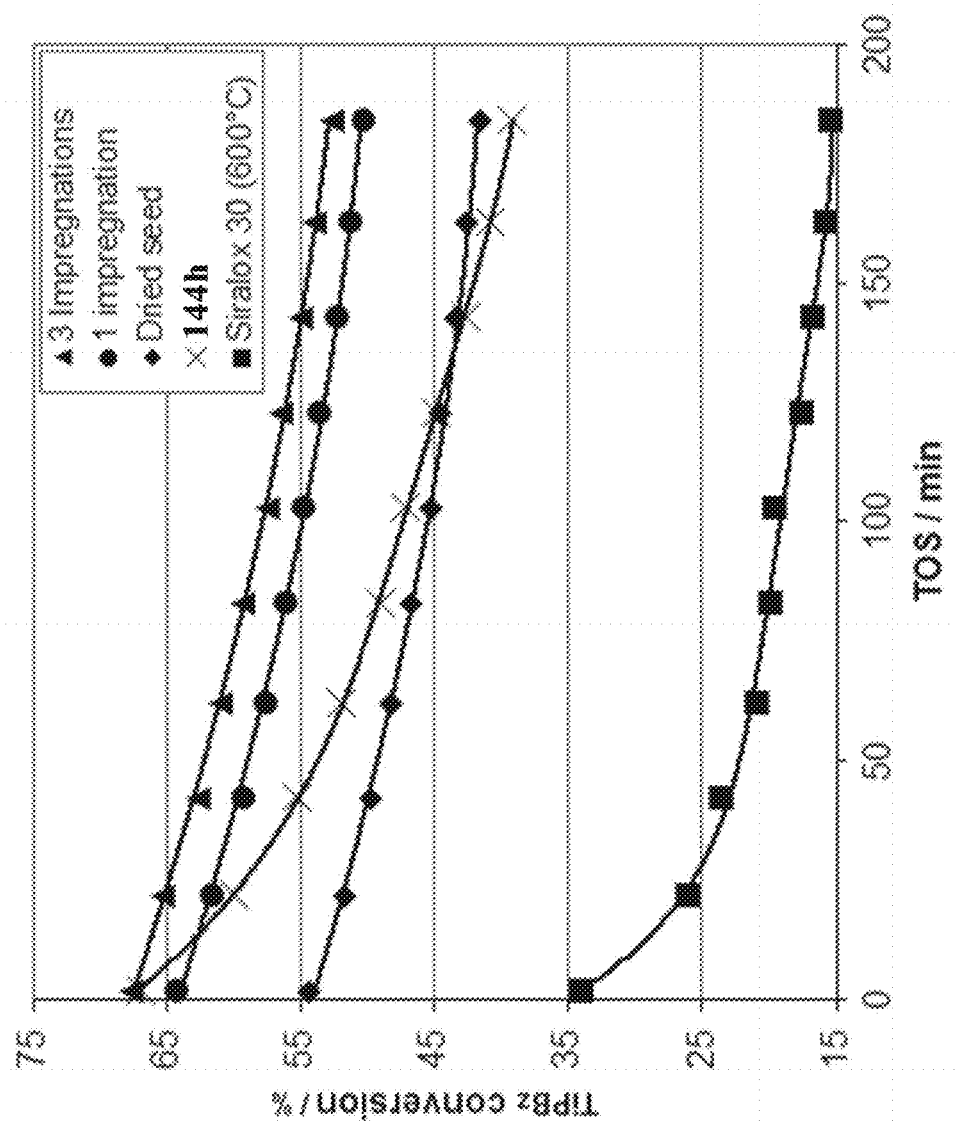
FIG. 8 presents the catalytic tests of the solids prepared according to example 1, 3 and 4.

FIG. 8 presents the catalytic tests of the solids prepared according to example 1, 3 and 4

Figure 9:
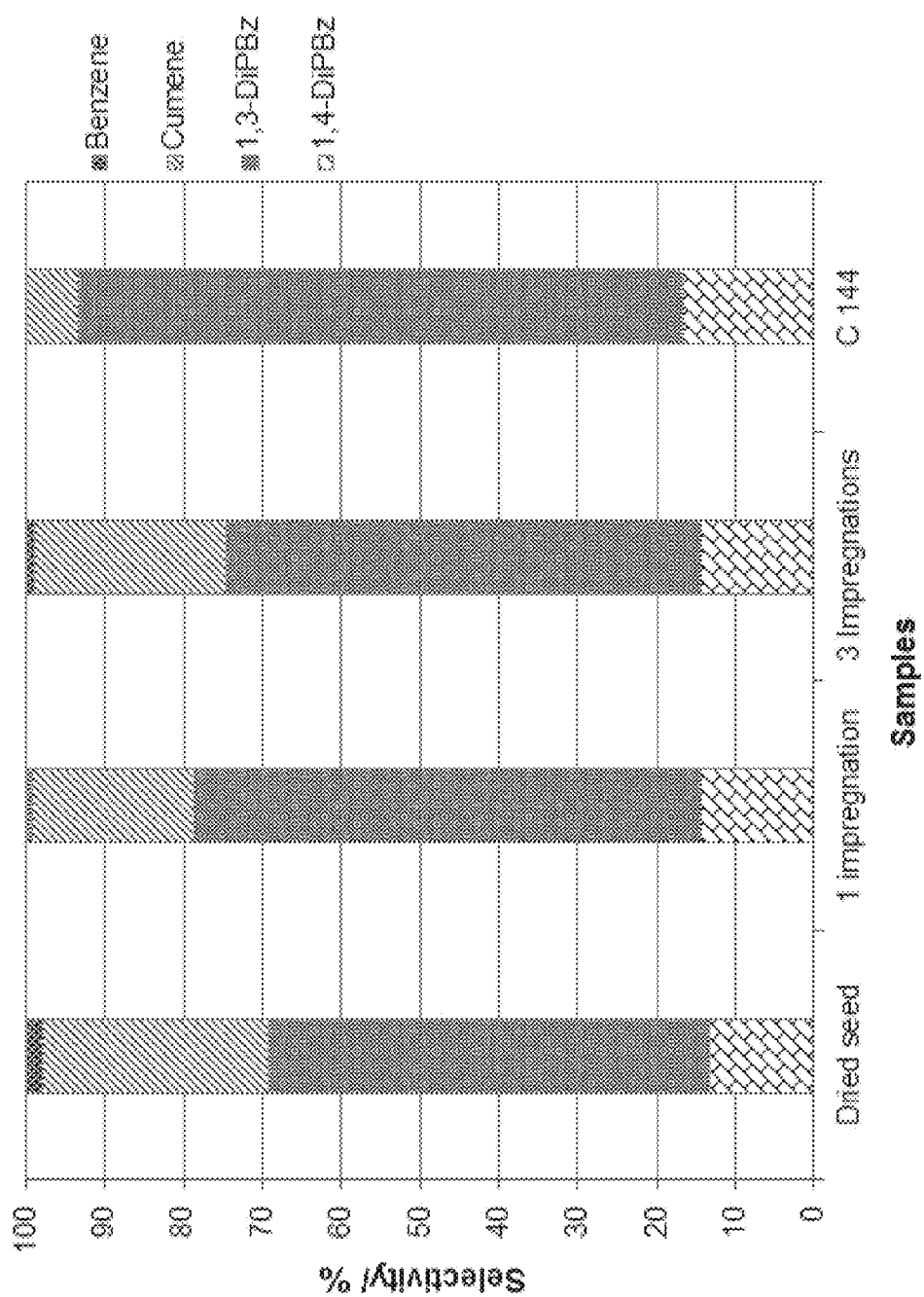
FIG. 9 presents the detailed selectivity of the catalytic tests of the solids prepared according to example 4.

FIG. 9 presents the detailed selectivity of the catalytic tests of the solids prepared according to example 4

Figure 10:
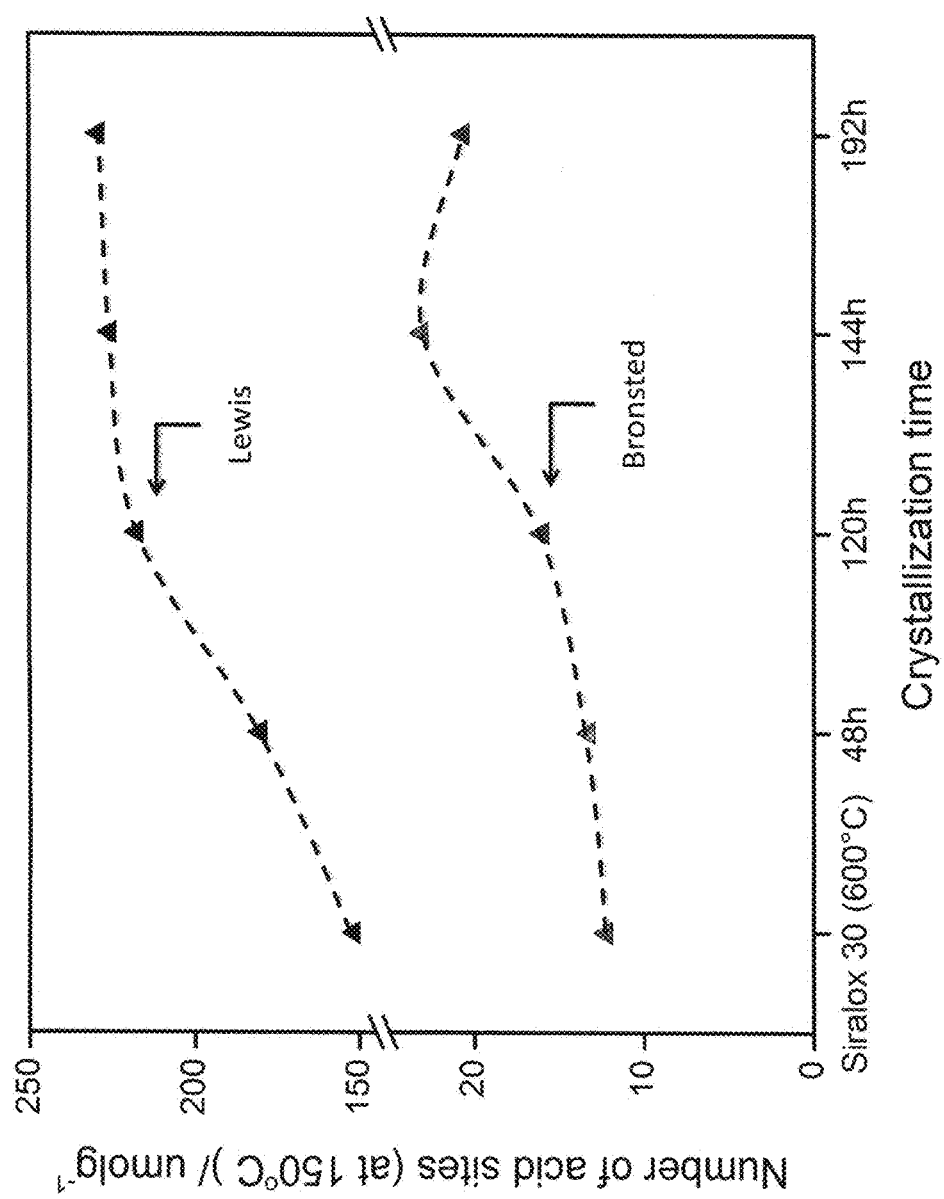
FIG. 10 presents a correlation of the number of acidic sites measured via pyridine adsorption as function of the crystallization time.
Figure 11:
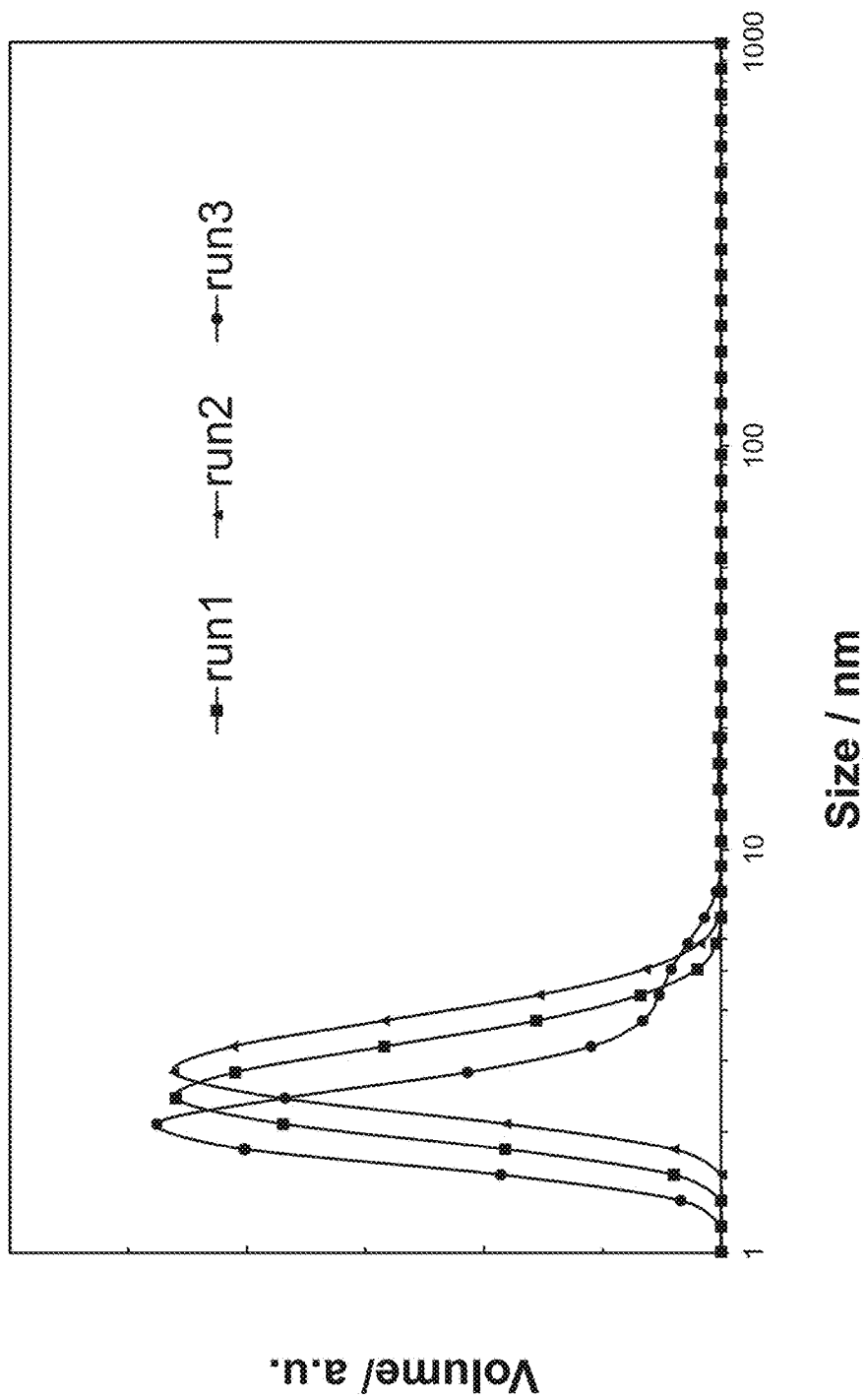
FIG. 11 presents a size of crystal of molecular sieve in solution after various tests measured via Dynamic Light Scattering (DLS).

FIG. 10 correlation of the number of acidic sites measured via pyridine adsorption as function of the crystallization time FIG. 11 size of crystal of molecular sieve in solution after various tests measured via Dynamic Light Scattering (DLS)

Figure 12:
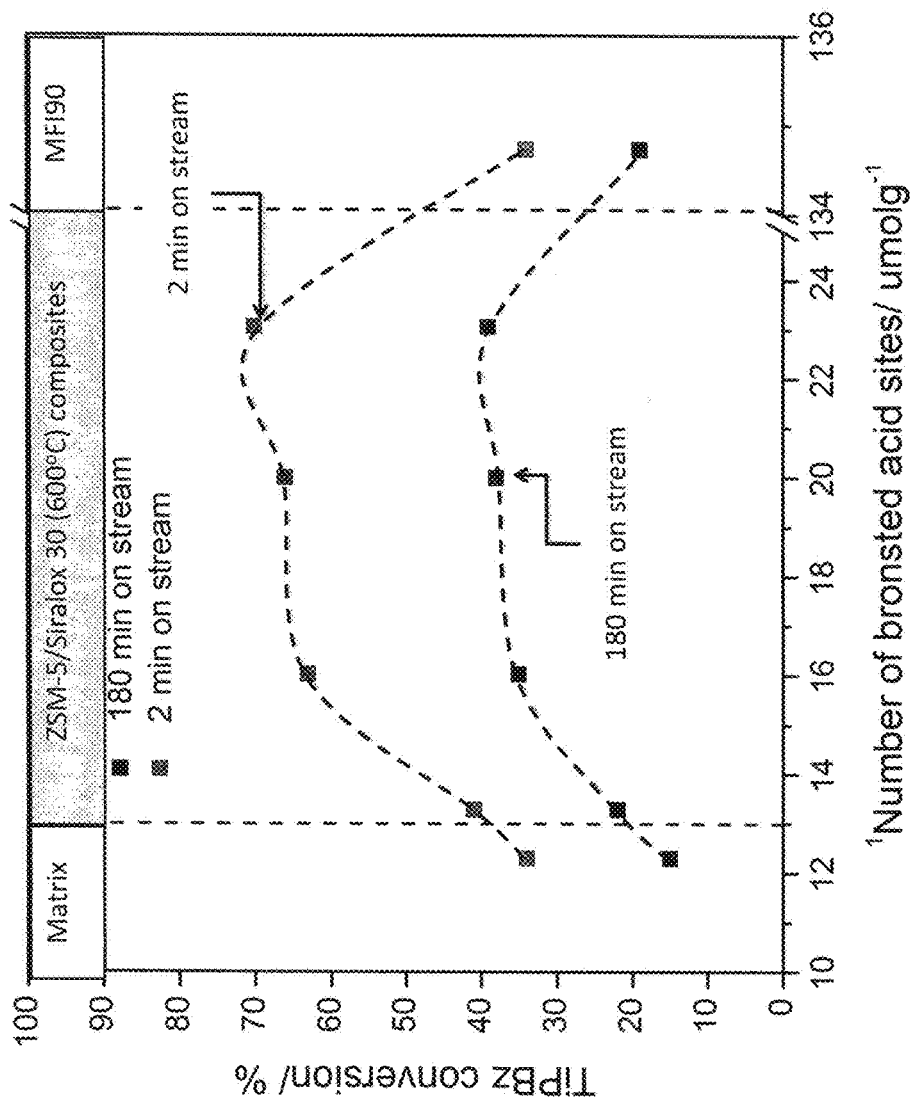
FIG. 12 presents conversion of TiPBz as function of the number of Bronsted acidic sites measure by pyridine adsorption.

FIG. 12 Conversion of TiPBz as function of the number of Bronsted acidic sites measure by pyridine adsorption. The conversion was measured after 2 min on stream and after 180 min on stream (the catalyst slightly deactivated after 180 min on stream). On the right site of the graph the conversion of TiPBz is presented for the Siralox 300 without deposition of the crystal of molecular sieve. On the left side of the graph the conversion for nanosized commercial crystals of ZSM-5 are presented.

Figure 13:
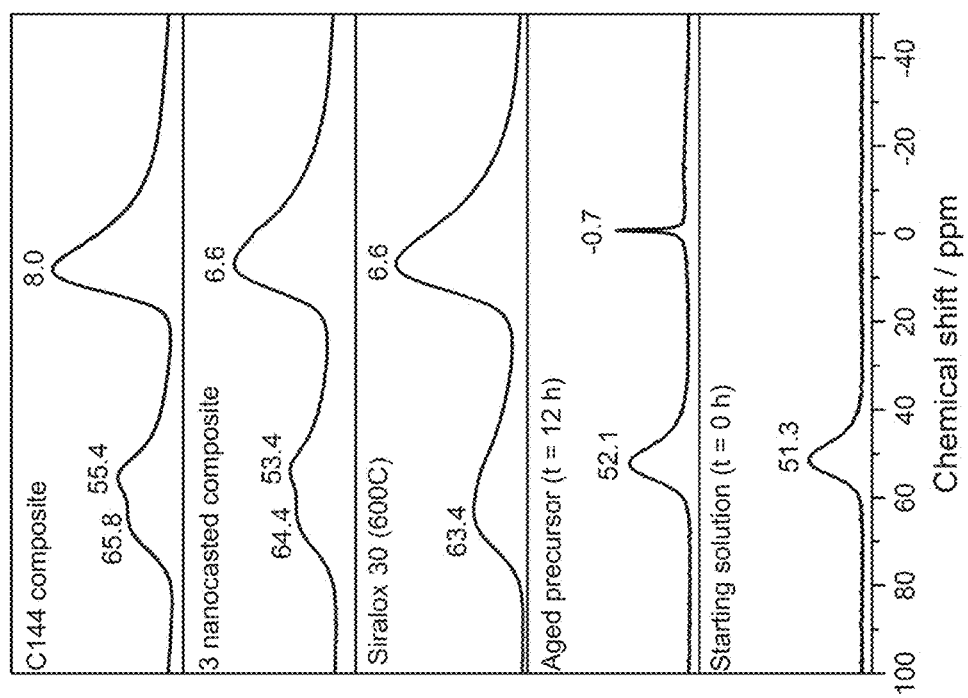
FIG. 13 presents $^{27}Al$ MAS NMR spectra according to example 7.

FIG. 13 $^{27}Al$ MAS NMR spectra according to example 7 of the starting solution, the aged solution after 12 h, the matrix on which the siralox 30 is deposited, the matrix being deposited three times with the solution containing the nano size crystal of molecular sieve (3 nanocasted composite). The spectra "C144 composite" related to the preparation according to example 2 with a maturation time of 144 h. The letter "t" stands for synthesis time.

EXAMPLES

Example 1 (According to Invention)—Preparation of the Catalyst Composition with a Precursor Solution being Maturated Before being Impregnated on Modified Porous Material A catalyst composition with a porous material being Siralox TH 30 (Sasol, Al2O3/SiO2-70/30 wt %) on which crystals of ZSM-5 molecular sieves are dispersed was prepared according to the following procedure.

The solution containing the precursor of molecular sieve (ZSM-5 precursor solution—4.5(TPA)$_2$O:25SiO$_2$:0.25Al$_2$O$_3$:430H$_2$O:Si/Al=50) was prepared by mixing TPAOH (tetrapropylazanium hydroxide; CAS [66082-78-8]), H$_2$O, Aluminium sulphate [10043-01-3], and TEOS (tetraethoxysilane; CAS [9044-80-8]). The ingredients were added gradually according to mention order and hydrolyzed at room temperature (RT) for 1 h with vigorous stirring and then closed and stirred for another 3 h. Prior to its use on the porous material, this solution was maturated at 100° C. for various maturation: 12 h, 36 h, 48 h, 72 h, 96 h, 120 h, 144 h. 168 h, 192 h.

The porous material used was commercial Siralox TH 30 a silica alumina oxide from Sasol in spray-dried form (~40-60 μm) with a Al$_2$O$_3$:SiO$_2$ ratio of 70:30. Prior to use, it was calcinated at 600° C. during 2 h. This calcination did not change the amorphous DRX signature of the Siralox 30 (see FIG. 1).

The size of the crystal of molecular sieves formed was measured via Dynamic Light Scattering (DLS) after 12 h of maturation at 100° C. The results are shown on FIG. 11. The measure was reproduced for the same sample three times (runs 1, 2 and 3). It appears that the size of the crystal measured is lower than 10 nm.

The 2.95 g of the calcined at 600° C. Siralox TH 30 was then impregnated with a 10 ml of 0.5 wt % solution of PDDA (Poly(diallyldimethylammonium chloride)). The mixture was stirred on a shaker at the speed of 175 rpm for 2 h at RT. Then the excess water was removed by evaporation overnight (on top of a 150° C. oven). The resulted solid was further dried at 100° C. for 15 min prior to be used in the synthesis. Then, the PDDA-impregnated Siralox TH 30 is added into the aged precursor solution (from 12 h to 192 h) and crystallization is carried out at 100° C. for 48 h (2 days). During this step, the precursors of the zeolite crystals in suspension in the solution are attracted and attached on the surface of the PDDA-impregnated Siralox TH 30.

The corresponding samples after the different crystallization times were separated from the solution by filtration followed by drying at 100° C. and calcination at 550° C. for 4 h to remove the template.

TABLE 1

Synthesis of ZSM-5/Siralox TH 30 (600° C.) composite

| Molar composition | ZSM-5 precursor solution = A + B + C + D | | | | |
|---|---|---|---|---|---|
| | A | B | C | D | E |
| Reagents | TPAOH 1M | TEOS | Aluminium sulphate | H$_2$O | Siralox TH 30 (600° C.) |
| Source of reagents | Alfa Aesar | Aldrich | Aldrich | Distilled water | SASOL |
| % purity | 20% | 98% | 98% | — | 30% SiO$_2$/ 70% Al$_2$O$_3$ |
| Molecular weight (g/mol) | 203 | 208 | 666 | 18 | — |
| Theoretical weight (g) | 15.252 | 8.858 | 0.2834 | 0.6984 | 0.5 |
| Measured weight (g) | 15.263 | 8.862 | 0.283 | 0.712 | 0.5 |

1. TPAOH, H$_2$O, Aluminium sulphate, and TEOS was added successively and hydrolyzed at RT for 1 h in an open bottle (50 mL) under vigorous stirring to facilitate hydrolysis. It was then closed and stirred for another 3 h at RT.
2. After that, the synthesis solution was transferred into a 125 mL Nalgene PP bottle and maturating was performed at 100° C. for 12 h, 24 h, 36 h, 48 h, 72 h, 96 h, 120 h, 144 h, 168 h, 192 h respectively.
3. After maturating, Siralox 30 (600° C.) which has been treated with PDDA was added into the synthesis solution and the mixture was stirred on a shaker at the speed of 125 rpm for 2 h at RT.
4. The crystallization was performed at 100° C. for 2 days.
5. After synthesis, the ZSM-5/Siralox 30 (600° C.) was treated under ultrasonic radiation for 3 min to disperse loosely attached crystals; washed under vacuum filtration until pH 8-9, dried at 100° C. followed by a calcinations at 550° C. for 4 h.

| Aging: | 12 h, 36 h, 48, 72 h, 96 h, 120 h, 144 h, 168 h, 192 h at 100° C. |
|---|---|
| ZSM-5 precursor solution appearance: | Transparent solution |

The samples are hereinafter identified as 12 h, 36 h, 48 h, 72 h, 96 h, 120 h, 144 h, 168 h, 192 h.

TABLE 2

Quantification of the crystals of molecular sieves deposited on the porous materials after various crystallization times (Zeolite/Siralox TH 30 (600° C.) composite after Na$^+$ exchange (TG data)).

| Crystallization time, t/h | Weight loss, W/% | Wt % active phase |
|---|---|---|
| 0 | 1.457 | — |
| 12 | 1.876 | 4.2 |
| 24 | 2.172 | 7.2 |
| 36 | 2.261 | 8.0 |
| 48 | 2.300 | 8.4 |
| 60 | 2.347 | 8.9 |
| 72 | 2.458 | 10.0 |
| 96 | 2.987 | 15.3 |
| 120 | 2.500 | 16.8 |
| 144 | 3.297 | 18.4 |

TABLE 2-continued

Quantification of the crystals of molecular sieves deposited on the porous materials after various crystallization times (Zeolite/Siralox TH 30 (600° C.) composite after Na+ exchange (TG data)).

| Crystallization time, t/h | Weight loss, W/% | Wt % active phase |
|---|---|---|
| 168 | 3.630 | 21.7 |
| 192 | 3.474 | 20.2 |

TABLE 3

BET surface area of the catalyst composition

| Samples | $S_{BET}$/m$^2$g$^{-1}$ | $S_{EXT}$/m$^2$g$^{-1}$ | $V_{mic}$/cm$^3$g$^{-1}$ | $V_{meso}$/cm$^3$g$^{-1}$ |
|---|---|---|---|---|
| Siralox 30 (600° C.) | 322 | 227 | 0.00 | 1.00 |
| 12 h | 317 | 232 | 0.03 | 1.20 |
| 144 h | 397 | 316 | 0.04 | 1.22 |
| 168 h | 414 | 320 | 0.04 | 1.22 |
| 192 h | 419 | 316 | 0.05 | 1.20 |

TABLE 4

TPD NH3 of the catalyst composition

| Samples | TPD NH3/μmol/g | % |
|---|---|---|
| Siralox 30 (600° C.) | 297 | 100 |
| 72 h | 402 | 135 |
| 144 h | 487 | 167 |

The XRD spectra do not evidence any crystals of molecular sieve. However those crystals are evidenced by indirect techniques, in particular by surface area measurements. An increase of the surface area is evidenced whereas there is only a very little increase of the microporous volume (from 0.03 to 0.05 cm$^3$ g$^{-1}$). Such an increase of the surface area is an evidence of presence of small size crystal on the porous material. It can therefore be concluded that the crystals are too small to be detected via XRD. The detection limit of the crystal size by XRD being of 50 nm, the crystals of molecular sieves are smaller than 50 nm. The NMR $^{13}$C spectra show that the signature of the template is similar to a signature of the template inside ZSM-5 crystal. There is therefore deposition of crystals of ZSM-5 on the porous support.

Both the Bronsted and Lewis concentration of acidic site was measured using pyridine adsorption at 150° C. The results obtained are displayed on FIG. 10. It appears that the number of both Bronsted and Lewis acidic site significantly increases with the crystallization i.e. with the quantity of crystal of molecular sieve deposited on siralox 30. Bronsted acidic site concentration of up to 20 μmol/g was obtained with a crystallization time of 144 h.

Example 2 (According to Invention)—Catalytic Tests of Materials Prepared According to Example 1

Catalytic tests of cracking of the TiPBz were performed on the catalyst composition prepared (see FIG. 4). It appears that the catalyst compositions prepared with a longer crystallisation time (more than 36 h) have a higher activity than the initial Siralox TH 30 (600° C.). Without willing to be bound to any theory, it is interpreted that the catalysts with longer crystallisation time have more acid sites and more developed surface area (table 3-4). This higher acidity originates from the small crystals of molecular sieve deposited on the surface of the Siralox TH 30. The catalyst compositions prepared by deposition of the crystal of molecular crystals on Siralox TH 30 present a higher conversion than the Siralox TH 30.

Example 3 (Comparative) Preparation of the Catalyst Composition with a Precursor Solution being Maturated Followed by Drying and Calcinations. No Contact with the Porous Material Molecular sieve precursor solution was prepared by mixing TPAOH (tetrapropylazanium hydroxide; CAS [66082-78-8]), H$_2$O, Aluminium sulphate, and TEOS (tetraethoxysilane; CAS [9044-80-8]). The ingredients were added successively according to mentioned order and hydrolyzed at RT for 3 h with vigorous stirring. Prior to its use, this solution was maturated at 100° C. for 12 h. Dynamic Light Scattering (DLS) shows that particles smaller than 10 nm with a narrow particle size distribution are present in the seed solution aged for 12 h at 100° C. The catalyst composition was prepared by evaporating of the solution followed by at 100° C. and calcinations at 550° C. for 4 h. The sample is hereinafter identified as Dried Seed.

Example 4 (According to Invention)—Preparation of the Catalyst Composition with a Precursor Solution being Maturated Before being Impregnated on Modified Porous Material with One or More than One Impregnations A series of catalyst compositions with a porous material being Siralox TH 30 (Sasol) on which crystal of molecular sieves are dispersed by repeating the deposition step.

ZSM-5 precursor solution was prepared by mixing TPAOH (tetrapropylazanium hydroxide; CAS [66082-78-8]), H$_2$O, Aluminium sulphate, and TEOS (tetraethoxysilane; CAS [9044-80-8]). The ingredients were added successively according to mentioned order and hydrolyzed at RT for 3 h with vigorous stirring. Prior to its use, this solution was maturated at 100° C. for 12 h. Dynamic Light Scattering (DLS) shows that particles smaller than 10 nm with a narrow particle size distribution are present in the seed solution aged for 12 h at 100° C.

The porous material used was commercial Siralox TH 30 a silica alumina oxide from Sasol with a Al$_2$O$_3$:SiO$_2$ ratio of 70:30. Prior to use, it was calcinated at 600° C. during 2 h. This calcination did not change the amorphous XRD signature of the Siralox 30 (see FIG. 5).

In order to obtain the PDDA-modified Siralox 30, 2.95 g of the calcined at 600° C. Siralox 30 was impregnated with a 10 ml of 0.5 wt % solution of PDDA (Poly(diallyldimethylammonium chloride)). The mixture was stirred on a shaker at the speed of 175 rpm for 2 h at RT. Then the excess water was removed by evaporation overnight (on top of a 150° C. oven). The resulted solid was further dried at 100° C. for 15 min prior to be used in the synthesis. The Siralox TH 30 once impregnated with PDDA was then impregnated with 1 g of ZSM-5 precursor solution added drop wise to 0.5 g of the impregnated Siralox 30. The mixture obtained was then dried overnight in open air and then at 100° C. for 2 h.

Then, the impregnation of ZSM-5 precursor solution is repeated up to three times using the same procedure. Before characterisation, the solid was calcinated under air at 550° C. for 4 h.

The solids hence prepared were characterized via DRX (see FIG. 5). The DRX patterns show that the solid conserves an amorphous pattern. Similarly the dried seed also have an amorphous DRX pattern.

The SEM micrographs of the material prepared (see FIG. 6) demonstrate that the matrix of Siralox TH 30 is covered with seeds of an average diameter of about 10 nm. SEM investigation also shows a random shape and size of the aggregates obtained by drying of seed particles. The SEM micrograph in FIG. 6 illustrates that after three impregnations with ZSM-5 precursor solution, the surface of Siralox TH 30 (600° C.) matrix is covered by crystals of seeds.

The adsorption of pyridine was also measured (see FIG. 7) demonstrating that the number of acidic sites increase with the number of impregnation. There is therefore an increase of the amount of active phase present.

The samples are hereinafter identified as "1 impregnation" or "3 impregnations"

Example 5—Catalytic Test of Materials Prepared According to Example 3

Catalytic tests of cracking of the TiPBz were performed on the catalyst composition prepared (see FIG. 8). Even the material prepared by one impregnation of the Siralox TH 30 shows higher activity than the dried seeds (comparative example) and the Siralox TH 30 without impregnation. The material prepared according to example 1 shows also higher activity than the dried seeds (comparative example). The technical advantage of dispersing such seeds on a porous material is therefore higher activity and easy handling the seeds-containing materials. In addition, having the active sites dispersed on such matrix also allows an easier formulation of the material.

The selectivity of the catalysts in TiPBz cracking is displayed on FIG. 9. With the catalyst impregnated three times (example 3), the selectivity toward benzene and cumene is higher relative to the sample prepared according to example 1. This means that different preparation procedure allows adjusting catalyst design toward selectivity to secondary cracking reaction.

The impact of the quantity of acidic Bronsted sites on the conversion of TiPBZ is displayed on FIG. 12. It appears that when the concentration of Bronsted site increases, the conversion of TiPBZ increases. There is therefore an advantage in using the catalyst composition prepared according to the example compared with pure Siralox 30. When pure MFI-90 (ZSM-5) is used, the number of Bronsted acidity sites is significantly higher, but the conversion decreases. This is due to the low accessibility of the acidity sites when pure MFI-90 is used. The composition according to the invention therefore allows increasing the conversion of bulky molecules like TiPBZ.

Example 6 (According to Invention)—On Extruded Body Treatment

Preparation of the catalyst composition with a precursor solution being maturated before being impregnated on modified porous material.

A catalyst composition with a porous material being extruded 1.5 mm cylinders Siralox 30 (Sasol, Al2O3/SiO2—70/30 wt %) on which crystals of ZSM-5 molecular sieves are dispersed was prepared according to the procedure described in example 1 using 144 h maturation time. The sample on which the ZSM-5 is impregnated has the suffix—C144. 5 g of sample was used for synthesis and the amount of the reagent was adjusted proportionally to the amount of the support. The surface area and the acidic sites measured on the catalyst composition obtained are summarized in table 5.

TABLE 5

Extruded Siralox 30 impregnated with crystals of ZSM-5 molecular sieve.

| | SBET, cm3/g | Vmicro, cm3/g | Acid sites, TPD NH3, µmol/g |
|---|---|---|---|
| Siralox 30, 1.5 mm cylinders | 284 | 0.001 | 414 |
| Siralox 30, 1.5 mm cylinders - C144 | 375 | 0.029 | 505 |

It appears that the impregnation of crystal of ZSM-5 according to the invention allows increasing the surface area of the already shaped catalyst.

Example 7—Characterization of the Various Catalysts by $^{27}$Al MAS NMR

The catalyst compositions were also characterized via $^{27}$Al MAS NMR. Indeed $^{27}$Al MAS NMR allows determining the coordination and the local structure of aluminium species in zeolites since each $^{27}$Al site can be readily resolved based on their distinctly different chemical shifts (5). FIG. 13 shows the $^{27}$Al MAS NMR spectra of the composites and its precursors. The $^{27}$Al NMR spectrum of the starting solution shows a signal of 51.3 ppm characteristic peak of tetrahedrally coordinated aluminium ($Al^{IV}$) in which the aluminium atoms are integrated within the siliceous tetrahedral lattice with four fold coordination. After 12 h aging at 100° C., some octahedrally coordinated aluminium (Al) is also present in the aged precursor as indicated by the peak with chemical shift ca. −0.7 ppm.

The $^{27}$Al NMR spectrum of the parent matrix (Siralox 30; 600° C.) shows signals at 6.6 and 63.4 ppm which are attributed to octahedrally and tetrahedrally coordinated Al atoms, respectively. The $^{27}$Al NMR spectra of the catalyst compositions (C144 and 3 nanocasted composite) exhibit some differences compared to the spectrum of the parent matrix; the signal of the tetrahedrally coordinated aluminium is shifted to higher field.

The nanocasted composites shows a broad low-intensity $Al^{IV}$ peak at δ=53.4 ppm, which evolves with the crystallization time (i.e. 6 days or 144 h), shifting toward δ=55.4; the latter peaks present an outline sharper than the former peak, thus indicating a more defined coordination of Al atom into zeolite lattice, which is a consequence of the crystallite growth in C144 composite.

The crystals of molecular sieves deposited on the siralox matrix cannot be evidenced by XRD. They are indeed too small to being detected via XRD. However they can be evidence via $^{27}$Al NMR as the $Al^{IV}$ peak at δ=53.4 ppm demonstrates the presence of tetrahedrally coordinated aluminium Al characteristic of crystallized molecular sieve.

The increase of surface area, the absence of XRD signature and the presence of tetrahedrally coordinated aluminium demonstrate that very small crystal of molecular sieve are deposited on the surface of the siralox matrix.

The invention claimed is:

1. A catalyst composition comprising an inorganic porous material with pore diameters of at least 2 nm and crystals of molecular sieve;

wherein the crystals of molecular sieve have an average diameter not bigger than 50 nm measured using Scanning Electron Microscopy, wherein the crystals of molecular sieve comprise a zeolite selected from the group consisting of MOR, FAU, EMM, MWW, BETA, ZSM-21, ZSM-42, AEI, CHA, ERI, LEV, OFF, ZSM-34, AFI, AEL, LTL, MFI (ZSM-5, silicalite, TS-1), MEL (ZSM-11, silicalite-2, TS-2), MTT (ZSM-23, EU-13, ISI-4, KZ-1), MFS (ZSM-57), HEU (Clinoptilolite), FER (ZSM-35, Ferrierite, FU-9, ISI-6, NU-23, Sr-D), TON (ZSM-22, Theta-1, ISI-1, KZ-2 and NU-10), LTL (L), MAZ (mazzite, Omega, ZSM-4) and mixtures thereof;

wherein the catalyst composition has a concentration of acid sites ranging from 50 to 1200 μmol/g measured by Temperature-Programmed Desorption of ammonia, TPD NH3; and wherein an X-ray diffraction pattern of the catalyst composition is the same as an X-ray diffraction pattern of the inorganic porous material.

2. The catalyst composition according to claim 1, further characterized in that the catalyst composition contains a Bronsted aciditic sites concentration of at least 10 μmol/g measured by pyridine desorption at 150° C.

3. The catalyst composition according to claim 1, further characterized in that the inorganic porous material is amorphous.

4. The catalyst composition according to claim 1, further characterized in that the catalyst composition contains up to 30 weight % of crystals of molecular sieve relative to a total weight of the catalyst composition.

5. The catalyst composition according to claim 1, further characterized in that the surface area is of at least 250 m²/g measured using ASTM D3663.

6. The catalyst composition according to claim 1, further characterized in that the ratio $V_{total}/V_{micro}$ is of at least 5, wherein $V_{total}$ is the total porous volume of the catalyst composition and $V_{micro}$ is the microporous volume of the catalyst composition, and wherein $V_{total}$ and $V_{micro}$ are measured via ASTM D4365.

7. The catalyst composition according to claim 1, further characterized in that the inorganic porous material has pores with a mesoporous volume and/or macroporous volume, and the crystals of molecular sieve have pores with a microporous volume, wherein a ratio of the microporous volume over the mesoporous and/or macroporous volume ranges from 0.2 to 0.005, and wherein the mesoporous volume and/or macroporous volume and the microporous volume are determined using ASTM D4365.

8. The catalyst composition according to claim 1, characterized in that the catalyst composition further comprises one or more of:
phosphorus;
at least one metal selected from the group consisting of: B, Cr, Co, Ga, Fe, Li, Mg, Ca, Mn, La, Ti, Mo, W, Ni, Ag, Sn or Zn, Pt, Pd, Ru, Re, Os, Au, and combinations thereof;
at least one binder selected from the group consisting of: silica, silica alumina, metal silicates, metal oxides and/or metals, amorphous alumophophate or silica alumophosphates, gels including mixtures of silica and metal oxides, and combinations thereof.

9. The catalyst composition according to claim 1, wherein the crystals of molecular sieve have a pore diameter smaller than 2 nm.

10. The catalyst composition according to claim 1, further characterized in that the crystals of molecular sieve are of WI type.

11. The catalyst composition according to claim 1, further characterized in that the inorganic porous material is:
a silica alumina, a $SiO_2$, a $Al_2O_3$ or a mixture of thereof; or
an amorphous inorganic material containing $Al_2O_3$ and $SiO_2$ with an atomic ratio Al/Si >1.

12. The catalyst composition of claim 11, wherein the inorganic porous material is the amorphous inorganic material containing $Al_2O_3$ and $SiO_2$ with an atomic ratio Al/Si>1, and wherein the amorphous inorganic material contains elements different from Si, O, Al at a concentration below 500 ppm weight.

* * * * *